(12) United States Patent
Yang

(10) Patent No.: US 11,396,537 B2
(45) Date of Patent: Jul. 26, 2022

(54) POLYPEPTIDE, PROCESS FOR THE PRODUCTION THEREOF AND USE THEREOF

(71) Applicant: Shanxi Jinbo Bio-Pharmaceutical Co., Ltd., Shanxi (CN)

(72) Inventor: Xia Yang, Shanxi (CN)

(73) Assignee: Shanxi Jinbo Bio-Pharmaceutical Co., Ltd., Shanxi (CN)

( * ) Notice: Subject to any disclaimer, the term of this patent is extended or adjusted under 35 U.S.C. 154(b) by 163 days.

(21) Appl. No.: 16/698,206

(22) Filed: Nov. 27, 2019

(65) Prior Publication Data

US 2020/0165319 A1 May 28, 2020

(30) Foreign Application Priority Data

Nov. 28, 2018 (CN) .......................... 201811438582.6

(51) Int. Cl.
| | | |
|---|---|---|
| *C07K 14/78* | (2006.01) | |
| *C07K 1/14* | (2006.01) | |
| *C07K 1/18* | (2006.01) | |
| *C12N 15/70* | (2006.01) | |
| *A61K 38/00* | (2006.01) | |

(52) U.S. Cl.
CPC .............. *C07K 14/78* (2013.01); *C07K 1/145* (2013.01); *C07K 1/18* (2013.01); *C12N 15/70* (2013.01)

(58) Field of Classification Search
CPC ..................................................... C07K 16/18
See application file for complete search history.

(56) References Cited

U.S. PATENT DOCUMENTS

| | | | | |
|---|---|---|---|---|
| 2006/0008905 A1* | 1/2006 | Mattern | .................. | A61L 27/60 435/395 |
| 2007/0264277 A1* | 11/2007 | Behrens | .................. | A61P 37/02 424/185.1 |
| 2010/0322908 A1* | 12/2010 | Everland | .................. | A61L 27/56 424/93.7 |
| 2014/0073575 A1* | 3/2014 | Hennet | .................. | C07K 14/78 514/17.2 |

FOREIGN PATENT DOCUMENTS

| | | | | |
|---|---|---|---|---|
| CN | 103122027 A | 5/2013 | | |
| CN | 108822209 A | 11/2018 | | |
| CN | 109593126 A | 4/2019 | | |
| EP | 2976352 A1 | 1/2016 | | |
| EP | 3660045 A1 * | 6/2020 | ............ | C07K 1/145 |
| WO | 2014/146175 A1 | 9/2014 | | |

OTHER PUBLICATIONS

Translated CN-103122027-A (Oct. 12, 2021) pp. 1-14.*
Hua et al. (2018) Functional enhancement of neuronal cell behaviors and differentiation by elastin-mimetic recombinant protein presenting Arg-Gly-Asp peptides,, Biochem. Biophys. Res. Commun., vol. 508, pp. 1018-1023.*
Han et al., Assessment of prokaryotic collagen-like sequences derived from streptococcal Scl1 and Scl2 proteins as a source of recombinant GXY polymers. Appl Microbiol Biotechnol. Aug. 2006;72(1):109-115.
Hua et al., Characterization by high-resolution crystal structure analysis of a triple-helix region of human collagen type III with potent cell adhesion activity. Biochem Biophys Res Commun. Jan. 22, 2019;508(4):1018-1023.
Peng et al., Constructs for the expression of repeating triple-helical protein domains. Biomed Mater Feb. 2009;4(1):015006, 8 pages.
Yao et al.. Design, expression and characterization of collagen-like proteins based on the cell adhesive and crosslinking sequences derived from native collagens. J Biochem. Nov. 2004;136(5):643-9.
Zhang, A Study for TEV enzyme fusion expression in *Escherichia coli* and its activity analysis method. Master Degree Thesis. College of Life Science, South China Agricultural University. 68 pages. May 2016.
European Office Action for Application No. 19211389.2, dated Mar. 27, 2020, 10 pages.

* cited by examiner

*Primary Examiner* — Manjunath N Rao
*Assistant Examiner* — Samuel W Liu
(74) *Attorney, Agent, or Firm* — McCarter & English, LLP; Yu Lu

(57) ABSTRACT

The present invention relates to a polypeptide, a process for the production thereof and a use thereof. The polypeptide of the present invention has excellent adhesion effect and is highly stable in an aqueous solution. Endotoxins can be more easily removed from the product of the polypeptide.

8 Claims, 5 Drawing Sheets

Specification includes a Sequence Listing.

```
                         SEQUENCE LISTING

<160> NUMBER OF SEQ ID NOS: 13

<210> SEQ ID NO 1
<211> LENGTH: 30
<212> TYPE: PRT
<213> ORGANISM: Homo sapiens

<400> SEQUENCE: 1

Gly Glu Arg Gly Ala Pro Gly Phe Arg Gly Pro Ala Gly Pro Asn Gly
1               5                   10                  15

Ile Pro Gly Glu Lys Gly Pro Ala Gly Glu Arg Gly Ala Pro
            20                  25                  30

<210> SEQ ID NO 2
<211> LENGTH: 10
<212> TYPE: PRT
<213> ORGANISM: artifical sequence
<220> FEATURE:
<223> OTHER INFORMATION: the C terminal sequence

<400> SEQUENCE: 2

Gly Pro Pro Gly Pro Cys Cys Gly Gly Gly
1               5                   10

<210> SEQ ID NO 3
<211> LENGTH: 480
<212> TYPE: PRT
<213> ORGANISM: artifical sequence
<220> FEATURE:
<223> OTHER INFORMATION: TE16C

<400> SEQUENCE: 3

Gly Glu Arg Gly Ala Pro Gly Phe Arg Gly Pro Ala Gly Pro Asn Gly
1               5                   10                  15

Ile Pro Gly Glu Lys Gly Pro Ala Gly Glu Arg Gly Ala Pro Gly Glu
            20                  25                  30

Arg Gly Ala Pro Gly Phe Arg Gly Pro Ala Gly Pro Asn Gly Ile Pro
        35                  40                  45

Gly Glu Lys Gly Pro Ala Gly Glu Arg Gly Ala Pro Gly Glu Arg Gly
    50                  55                  60

Ala Pro Gly Phe Arg Gly Pro Ala Gly Pro Asn Gly Ile Pro Gly Glu
65                  70                  75                  80

Lys Gly Pro Ala Gly Glu Arg Gly Ala Pro Gly Glu Arg Gly Ala Pro
                85                  90                  95

Gly Phe Arg Gly Pro Ala Gly Pro Asn Gly Ile Pro Gly Glu Lys Gly
            100                 105                 110

Pro Ala Gly Glu Arg Gly Ala Pro Gly Glu Arg Gly Ala Pro Gly Phe
        115                 120                 125

Arg Gly Pro Ala Gly Pro Asn Gly Ile Pro Gly Glu Lys Gly Pro Ala
    130                 135                 140

Gly Glu Arg Gly Ala Pro Gly Glu Arg Gly Ala Pro Gly Phe Arg Gly
145                 150                 155                 160
```

```
Pro Ala Gly Pro Asn Gly Ile Pro Gly Glu Lys Gly Pro Ala Gly Glu
            165                 170                 175
Arg Gly Ala Pro Gly Glu Arg Gly Ala Pro Gly Phe Arg Gly Pro Ala
            180                 185                 190
Gly Pro Asn Gly Ile Pro Gly Glu Lys Gly Pro Ala Gly Glu Arg Gly
            195                 200                 205
Ala Pro Gly Glu Arg Gly Ala Pro Gly Phe Arg Gly Pro Ala Gly Pro
210                 215                 220
Asn Gly Ile Pro Gly Glu Lys Gly Pro Ala Gly Glu Arg Gly Ala Pro
225                 230                 235                 240
Gly Glu Arg Gly Ala Pro Gly Phe Arg Gly Pro Ala Gly Pro Asn Gly
            245                 250                 255
Ile Pro Gly Glu Lys Gly Pro Ala Gly Glu Arg Gly Ala Pro Gly Glu
            260                 265                 270
Arg Gly Ala Pro Gly Phe Arg Gly Pro Ala Gly Pro Asn Gly Ile Pro
            275                 280                 285
Gly Glu Lys Gly Pro Ala Gly Glu Arg Gly Ala Pro Gly Glu Arg Gly
            290                 295                 300
Ala Pro Gly Phe Arg Gly Pro Ala Gly Pro Asn Gly Ile Pro Gly Glu
305                 310                 315                 320
Lys Gly Pro Ala Gly Glu Arg Gly Ala Pro Gly Glu Arg Gly Ala Pro
            325                 330                 335
Gly Phe Arg Gly Pro Ala Gly Pro Asn Gly Ile Pro Gly Glu Lys Gly
            340                 345                 350
Pro Ala Gly Glu Arg Gly Ala Pro Gly Glu Arg Gly Ala Pro Gly Phe
            355                 360                 365
Arg Gly Pro Ala Gly Pro Asn Gly Ile Pro Gly Glu Lys Gly Pro Ala
            370                 375                 380
Gly Glu Arg Gly Ala Pro Gly Glu Arg Gly Ala Pro Gly Phe Arg Gly
385                 390                 395                 400
Pro Ala Gly Pro Asn Gly Ile Pro Gly Glu Lys Gly Pro Ala Gly Glu
            405                 410                 415
Arg Gly Ala Pro Gly Glu Arg Gly Ala Pro Gly Phe Arg Gly Pro Ala
            420                 425                 430
Gly Pro Asn Gly Ile Pro Gly Glu Lys Gly Pro Ala Gly Glu Arg Gly
            435                 440                 445
Ala Pro Gly Glu Arg Gly Ala Pro Gly Phe Arg Gly Pro Ala Gly Pro
            450                 455                 460
Asn Gly Ile Pro Gly Glu Lys Gly Pro Ala Gly Glu Arg Gly Ala Pro
465                 470                 475                 480

<210> SEQ ID NO 4
<211> LENGTH: 6
<212> TYPE: PRT
<213> ORGANISM: artifical sequence
<220> FEATURE:
<223> OTHER INFORMATION: the N terminal sequence

<400> SEQUENCE: 4

Glu Asn Leu Tyr Phe Gln
1               5

<210> SEQ ID NO 5
<211> LENGTH: 486
<212> TYPE: PRT
<213> ORGANISM: artifical sequence
```

<220> FEATURE:
<223> OTHER INFORMATION: TE16C having the N terminal sequence

<400> SEQUENCE: 5

```
Glu Asn Leu Tyr Phe Gln Gly Glu Arg Gly Ala Pro Gly Phe Arg Gly
1               5                   10                  15

Pro Ala Gly Pro Asn Gly Ile Pro Gly Glu Lys Gly Pro Ala Gly Glu
            20                  25                  30

Arg Gly Ala Pro Gly Glu Arg Gly Ala Pro Gly Phe Arg Gly Pro Ala
        35                  40                  45

Gly Pro Asn Gly Ile Pro Gly Glu Lys Gly Pro Ala Gly Glu Arg Gly
    50                  55                  60

Ala Pro Gly Glu Arg Gly Ala Pro Gly Phe Arg Gly Pro Ala Gly Pro
65                  70                  75                  80

Asn Gly Ile Pro Gly Glu Lys Gly Pro Ala Gly Glu Arg Gly Ala Pro
                85                  90                  95

Gly Glu Arg Gly Ala Pro Gly Phe Arg Gly Pro Ala Gly Pro Asn Gly
            100                 105                 110

Ile Pro Gly Glu Lys Gly Pro Ala Gly Glu Arg Gly Ala Pro Gly Glu
        115                 120                 125

Arg Gly Ala Pro Gly Phe Arg Gly Pro Ala Gly Pro Asn Gly Ile Pro
    130                 135                 140

Gly Glu Lys Gly Pro Ala Gly Glu Arg Gly Ala Pro Gly Glu Arg Gly
145                 150                 155                 160

Ala Pro Gly Phe Arg Gly Pro Ala Gly Pro Asn Gly Ile Pro Gly Glu
                165                 170                 175

Lys Gly Pro Ala Gly Glu Arg Gly Ala Pro Gly Glu Arg Gly Ala Pro
            180                 185                 190

Gly Phe Arg Gly Pro Ala Gly Pro Asn Gly Ile Pro Gly Glu Lys Gly
        195                 200                 205

Pro Ala Gly Glu Arg Gly Ala Pro Gly Glu Arg Gly Ala Pro Gly Phe
    210                 215                 220

Arg Gly Pro Ala Gly Pro Asn Gly Ile Pro Gly Glu Lys Gly Pro Ala
225                 230                 235                 240

Gly Glu Arg Gly Ala Pro Gly Glu Arg Gly Ala Pro Gly Phe Arg Gly
                245                 250                 255

Pro Ala Gly Pro Asn Gly Ile Pro Gly Glu Lys Gly Pro Ala Gly Glu
            260                 265                 270

Arg Gly Ala Pro Gly Glu Arg Gly Ala Pro Gly Phe Arg Gly Pro Ala
        275                 280                 285

Gly Pro Asn Gly Ile Pro Gly Glu Lys Gly Pro Ala Gly Glu Arg Gly
    290                 295                 300

Ala Pro Gly Glu Arg Gly Ala Pro Gly Phe Arg Gly Pro Ala Gly Pro
305                 310                 315                 320

Asn Gly Ile Pro Gly Glu Lys Gly Pro Ala Gly Glu Arg Gly Ala Pro
                325                 330                 335

Gly Glu Arg Gly Ala Pro Gly Phe Arg Gly Pro Ala Gly Pro Asn Gly
            340                 345                 350

Ile Pro Gly Glu Lys Gly Pro Ala Gly Glu Arg Gly Ala Pro Gly Glu
        355                 360                 365

Arg Gly Ala Pro Gly Phe Arg Gly Pro Ala Gly Pro Asn Gly Ile Pro
    370                 375                 380

Gly Glu Lys Gly Pro Ala Gly Glu Arg Gly Ala Pro Gly Glu Arg Gly
385                 390                 395                 400
```

Ala Pro Gly Phe Arg Gly Pro Ala Gly Pro Asn Gly Ile Pro Gly Glu
                405                 410                 415

Lys Gly Pro Ala Gly Glu Arg Gly Ala Pro Gly Glu Arg Gly Ala Pro
            420                 425                 430

Gly Phe Arg Gly Pro Ala Gly Pro Asn Gly Ile Pro Gly Glu Lys Gly
            435                 440                 445

Pro Ala Gly Glu Arg Gly Ala Pro Gly Glu Arg Gly Ala Pro Gly Phe
450                 455                 460

Arg Gly Pro Ala Gly Pro Asn Gly Ile Pro Gly Glu Lys Gly Pro Ala
465                 470                 475                 480

Gly Glu Arg Gly Ala Pro
            485

<210> SEQ ID NO 6
<211> LENGTH: 501
<212> TYPE: PRT
<213> ORGANISM: artifical sequence
<220> FEATURE:
<223> OTHER INFORMATION: HC16

<400> SEQUENCE: 6

Gly Glu Arg Gly Ala Pro Gly Phe Arg Gly Pro Ala Gly Pro Asn Gly
1               5                   10                  15

Ile Pro Gly Glu Lys Gly Pro Ala Gly Glu Arg Gly Ala Pro Gly Glu
            20                  25                  30

Arg Gly Ala Pro Gly Phe Arg Gly Pro Ala Gly Pro Asn Gly Ile Pro
            35                  40                  45

Gly Glu Lys Gly Pro Ala Gly Glu Arg Gly Ala Pro Gly Glu Arg Gly
    50                  55                  60

Ala Pro Gly Phe Arg Gly Pro Ala Gly Pro Asn Gly Ile Pro Gly Glu
65                  70                  75                  80

Lys Gly Pro Ala Gly Glu Arg Gly Ala Pro Gly Glu Arg Gly Ala Pro
            85                  90                  95

Gly Phe Arg Gly Pro Ala Gly Pro Asn Gly Ile Pro Gly Glu Lys Gly
            100                 105                 110

Pro Ala Gly Glu Arg Gly Ala Pro Arg Ser Gly Glu Arg Gly Ala Pro
            115                 120                 125

Gly Phe Arg Gly Pro Ala Gly Pro Asn Gly Ile Pro Gly Glu Lys Gly
            130                 135                 140

Pro Ala Gly Glu Arg Gly Ala Pro Gly Glu Arg Gly Ala Pro Gly Phe
145                 150                 155                 160

Arg Gly Pro Ala Gly Pro Asn Gly Ile Pro Gly Glu Lys Gly Pro Ala
                165                 170                 175

Gly Glu Arg Gly Ala Pro Gly Glu Arg Gly Ala Pro Gly Phe Arg Gly
            180                 185                 190

Pro Ala Gly Pro Asn Gly Ile Pro Gly Glu Lys Gly Pro Ala Gly Glu
            195                 200                 205

Arg Gly Ala Pro Gly Glu Arg Gly Ala Pro Gly Phe Arg Gly Pro Ala
    210                 215                 220

Gly Pro Asn Gly Ile Pro Gly Glu Lys Gly Pro Ala Gly Glu Arg Gly
225                 230                 235                 240

Ala Pro Arg Ser Gly Glu Arg Gly Ala Pro Gly Phe Arg Gly Pro Ala
                245                 250                 255

Gly Pro Asn Gly Ile Pro Gly Glu Lys Gly Pro Ala Gly Glu Arg Gly
            260                 265                 270

```
Ala Pro Gly Glu Arg Gly Ala Pro Gly Phe Arg Gly Pro Ala Gly Pro
        275                 280                 285

Asn Gly Ile Pro Gly Glu Lys Gly Pro Ala Gly Glu Arg Gly Ala Pro
    290                 295                 300

Gly Glu Arg Gly Ala Pro Gly Phe Arg Gly Pro Ala Gly Pro Asn Gly
305                 310                 315                 320

Ile Pro Gly Glu Lys Gly Pro Ala Gly Glu Arg Gly Ala Pro Gly Glu
            325                 330                 335

Arg Gly Ala Pro Gly Phe Arg Gly Pro Ala Gly Pro Asn Gly Ile Pro
                340                 345                 350

Gly Glu Lys Gly Pro Ala Gly Glu Arg Gly Ala Pro Arg Ser Gly Glu
            355                 360                 365

Arg Gly Ala Pro Gly Phe Arg Gly Pro Ala Gly Pro Asn Gly Ile Pro
        370                 375                 380

Gly Glu Lys Gly Pro Ala Gly Glu Arg Gly Ala Pro Gly Glu Arg Gly
385                 390                 395                 400

Ala Pro Gly Phe Arg Gly Pro Ala Gly Pro Asn Gly Ile Pro Gly Glu
                405                 410                 415

Lys Gly Pro Ala Gly Glu Arg Gly Ala Pro Gly Glu Arg Gly Ala Pro
            420                 425                 430

Gly Phe Arg Gly Pro Ala Gly Pro Asn Gly Ile Pro Gly Glu Lys Gly
        435                 440                 445

Pro Ala Gly Glu Arg Gly Ala Pro Gly Glu Arg Gly Ala Pro Gly Phe
    450                 455                 460

Arg Gly Pro Ala Gly Pro Asn Gly Ile Pro Gly Glu Lys Gly Pro Ala
465                 470                 475                 480

Gly Glu Arg Gly Ala Pro Arg Ser Pro Glu Phe Gly Pro Pro Gly Pro
                485                 490                 495

Cys Cys Gly Gly Gly
            500

<210> SEQ ID NO 7
<211> LENGTH: 1458
<212> TYPE: DNA
<213> ORGANISM: artifical sequence
<220> FEATURE:
<223> OTHER INFORMATION: TE16C having the N terminal sequence

<400> SEQUENCE: 7
gaaaacctgt atttccaggg tgaacgtggt gcaccaggtt ttcgtggtcc ggcaggtccg      60
aatggaattc cgggtgagaa aggaccggct ggtgagcgtg gtgcgccggg tgaacgtgga     120
gcgcctggtt ttcgtggccc agcaggtccg aacggtattc ctggtgaaaa aggtccggcg     180
ggagagcgtg gtgcaccggg tgaacgcggt gcaccgggat ttcgtggtcc agcaggaccg     240
aatggtatcc ctggtgaaaa aggaccggca ggtgagcgtg gagcgccagg tgaacgtggc     300
gcaccgggtt ttcgtggacc ggcaggcccg aatggtattc cgggtgaaaa aggcccggca     360
ggtgaacgtg gtgccccggg tgaacgtggt gcgcctggat ttcgtggccc ggcaggaccg     420
aacggtatcc tggagaaaaa ggtcctgca ggtgagcgcg gtgcgccggg cgagcgtggt     480
gcccctggtt ttcgcggtcc ggcaggccct aatggtattc ctggagaaaa aggccctgca     540
ggtgaacgcg agcaccggg tgagcgtggc gcacctggtt ttcgtggtcc tgcaggcccg     600
aacggtattc cggcgaaaa aggtccagca ggtgaacgtg gtgctccggg tgaacgtggt     660
gcacctggat ttcgcggtcc tgctggtccg aatggtattc caggtgaaaa aggtccggca     720
```

```
ggagagcgtg gagcaccggg agaacgtggt gcaccgggct ttcgtggtcc ggccggtcct    780
aacggtatcc caggtgaaaa aggtccggcc ggcgagcgtg gcgcccctgg tgagcgtggt    840
gctcctggtt ttcgtggtcc ggctggtccg aacggaattc ctggtgagaa aggtccggct    900
ggcgaacgtg gtgcaccggg tgaacgtggt gcaccgggtt tccgtggtcc ggcgggtcct    960
aatggtatcc cgggtgaaaa aggtccggca ggtgaacgtg gtgcaccggg tgaacgtggt   1020
gcaccgggtt ttcgcggacc ggcaggacct aatggtattc cgggagaaaa aggacctgcg   1080
ggtgaacgtg gtgcaccggg tgaacgtggt gcaccgggtt ttcgtggtcc ggcaggtcct   1140 aatgaattc ctggagagaa aggacctgca ggtgaacgtg gtgcaccggg tgaacgtggt    1200
gcaccgggtt ttcgtggtcc ggcaggtcca atggtattc cgggtgaaaa aggtccggca    1260
ggtgaacgtg gtgcaccggg tgaacgtggt gcaccgggtt ttcgtggtcc ggcaggtccg   1320
aatggcattc ctggtgaaaa aggtccggca ggtgaacgtg gtgcaccggg tgaacgtggt   1380
gcaccgggtt ttcgtggtcc ggcaggtccg aatggtattc cgggtgaaaa aggtccggca   1440
ggtgaacgtg gtgcaccg                                                 1458
```

<210> SEQ ID NO 8
<211> LENGTH: 1503
<212> TYPE: DNA
<213> ORGANISM: artifical sequence
<220> FEATURE:
<223> OTHER INFORMATION: HC16

<400> SEQUENCE: 8

```
ggcgagcgtg gtgcacctgg ttttcgtggc cctgcaggcc cgaatggcat cccgggtgaa     60
aaaggcccgg caggcgaacg tggcgcccct ggtgaacgcg gcgcacctgg tttccgtggc    120
ccggcaggtc ctaacggtat cccgggcgaa aagggtcctg caggcgagcg tggcgccccg    180
ggtgaacgcg gtgcccctgg cttttcgcggt cctgccggcc ctaacggcat tccgggtgag    240
aaaggtcctg ccggtgagcg cggtgcccct ggtgagcgcg gcgcaccggg ctttcgtggc    300
ccggccggtc ctaatggtat tcctggcgag aagggtccgg caggtgaacg cggtgcacct    360
agatccggcg agcgtggtgc acctggtttt cgtggccctg caggcccgaa tggcatcccg    420
ggtgaaaaag gcccggcagg cgaacgtggc gcccctggtg aacgcggcgc acctggtttc    480
cgtggcccgc aggtcctaa cggtatcccg ggcgaaaagg gtcctgcagg cgagcgtggc    540
gccccgggtg aacgcggtgc ccctggcttt cgcggtcctg ccggccctaa cggcattccg    600
ggtgagaaag gtcctgccgg tgagcgcggt gcccctggtg agcgcggcgc accgggcttt    660
cgtggcccgg ccggtcctaa tggtattcct ggcgagaagg gtccggcagg tgaacgcggt    720
gcacctagat ccggcgagcg tggtgcacct ggttttcgtg gccctgcagg cccgaatggc    780
atcccgggtg aaaaaggccc ggcaggcgaa cgtggcgccc ctggtgaacg cggcgcacct    840
ggtttccgtg gcccggcagg tcctaacggt atcccgggca aaagggtcc tgcaggcgag    900 cgtggcgccc cgggtgaacg cggtgcccct ggctttcgcg gtcctgccgg ccctaacggc    960
attccgggtg agaaaggtcc tgccggtgag cgcggtgccc ctggtgagcg cggcgcaccg   1020
ggctttcgtg gcccggccgg tcctaatggt attcctggcg agaagggtcc ggcaggtgaa   1080
cgcggtgcac ctagatccgg cgagcgtggt gcacctggtt ttcgtggccc tgcaggcccg   1140
aatggcatcc cgggtgaaaa aggcccggca ggcgaacgtg gcgcccctgg tgaacgcggc   1200
gcacctggtt tccgtggccc ggcaggtcct aacggtatcc cgggcgaaaa gggtcctgca   1260
```

```
ggcgagcgtg gcgccccggg tgaacgcggt gcccctggct tcgcggtcc  tgccggccct    1320 aacggcattc cggtgagaa  aggtcctgcc ggtgagcgcg gtgccctgg  tgagcgcggc    1380 gcaccgggct tcgtggccc  ggccggtcct aatggtattc ctggcgagaa gggtccggca    1440
ggtgaacgcg gtgcaccta  gatctccggaa ttcggcccgc ctggtccttg ttgtggcggc   1500
ggc                                                                  1503
```

<210> SEQ ID NO 9
<211> LENGTH: 490
<212> TYPE: PRT
<213> ORGANISM: artifical sequence
<220> FEATURE:
<223> OTHER INFORMATION: T16a

<400> SEQUENCE: 9

```
Gly Glu Arg Gly Ala Pro Gly Phe Arg Gly Pro Ala Gly Pro Asn Gly
1               5                   10                  15

Ile Pro Gly Glu Lys Gly Pro Ala Gly Glu Arg Gly Ala Pro Gly Glu
            20                  25                  30

Arg Gly Ala Pro Gly Phe Arg Gly Pro Ala Gly Pro Asn Gly Ile Pro
        35                  40                  45

Gly Glu Lys Gly Pro Ala Gly Glu Arg Gly Ala Pro Gly Glu Arg Gly
    50                  55                  60

Ala Pro Gly Phe Arg Gly Pro Ala Gly Pro Asn Gly Ile Pro Gly Glu
65                  70                  75                  80

Lys Gly Pro Ala Gly Glu Arg Gly Ala Pro Gly Glu Arg Gly Ala Pro
                85                  90                  95

Gly Phe Arg Gly Pro Ala Gly Pro Asn Gly Ile Pro Gly Glu Lys Gly
            100                 105                 110

Pro Ala Gly Glu Arg Gly Ala Pro Gly Glu Arg Gly Ala Pro Gly Phe
        115                 120                 125

Arg Gly Pro Ala Gly Pro Asn Gly Ile Pro Gly Glu Lys Gly Pro Ala
    130                 135                 140

Gly Glu Arg Gly Ala Pro Gly Glu Arg Gly Ala Pro Gly Phe Arg Gly
145                 150                 155                 160

Pro Ala Gly Pro Asn Gly Ile Pro Gly Glu Lys Gly Pro Ala Gly Glu
                165                 170                 175

Arg Gly Ala Pro Gly Glu Arg Gly Ala Pro Gly Phe Arg Gly Pro Ala
            180                 185                 190

Gly Pro Asn Gly Ile Pro Gly Glu Lys Gly Pro Ala Gly Glu Arg Gly
        195                 200                 205

Ala Pro Gly Glu Arg Gly Ala Pro Gly Phe Arg Gly Pro Ala Gly Pro
    210                 215                 220

Asn Gly Ile Pro Gly Glu Lys Gly Pro Ala Gly Glu Arg Gly Ala Pro
225                 230                 235                 240

Gly Glu Arg Gly Ala Pro Gly Phe Arg Gly Pro Ala Gly Pro Asn Gly
                245                 250                 255

Ile Pro Gly Glu Lys Gly Pro Ala Gly Glu Arg Gly Ala Pro Gly Glu
            260                 265                 270

Arg Gly Ala Pro Gly Phe Arg Gly Pro Ala Gly Pro Asn Gly Ile Pro
        275                 280                 285

Gly Glu Lys Gly Pro Ala Gly Glu Arg Gly Ala Pro Gly Glu Arg Gly
    290                 295                 300

Ala Pro Gly Phe Arg Gly Pro Ala Gly Pro Asn Gly Ile Pro Gly Glu
305                 310                 315                 320
```

Lys Gly Pro Ala Gly Glu Arg Gly Ala Pro Gly Glu Arg Gly Ala Pro
            325                 330                 335

Gly Phe Arg Gly Pro Ala Gly Pro Asn Gly Ile Pro Gly Glu Lys Gly
            340                 345                 350

Pro Ala Gly Glu Arg Gly Ala Pro Gly Glu Arg Gly Ala Pro Gly Phe
            355                 360                 365

Arg Gly Pro Ala Gly Pro Asn Gly Ile Pro Gly Glu Lys Gly Pro Ala
        370                 375                 380

Gly Glu Arg Gly Ala Pro Gly Glu Arg Gly Ala Pro Gly Phe Arg Gly
385                 390                 395                 400

Pro Ala Gly Pro Asn Gly Ile Pro Gly Glu Lys Gly Pro Ala Gly Glu
            405                 410                 415

Arg Gly Ala Pro Gly Glu Arg Gly Ala Pro Gly Phe Arg Gly Pro Ala
            420                 425                 430

Gly Pro Asn Gly Ile Pro Gly Glu Lys Gly Pro Ala Gly Glu Arg Gly
            435                 440                 445

Ala Pro Gly Glu Arg Gly Ala Pro Gly Phe Arg Gly Pro Ala Gly Pro
        450                 455                 460

Asn Gly Ile Pro Gly Glu Lys Gly Pro Ala Gly Glu Arg Gly Ala Pro
465                 470                 475                 480

Gly Pro Pro Gly Pro Cys Cys Gly Gly Gly
            485                 490

<210> SEQ ID NO 10
<211> LENGTH: 1470
<212> TYPE: DNA
<213> ORGANISM: artifical sequence
<220> FEATURE:
<223> OTHER INFORMATION: T16a

<400> SEQUENCE: 10
ggtgaacgtg gtgcaccagg ttttcgtggt ccggcaggtc cgaatggaat tccgggtgag      60
aaaggaccgg ctggtgagcg tggtgcgccg ggtgaacgtg gagcgcctgg ttttcgtggc     120
ccagcaggtc cgaacggtat tcctggtgaa aaaggtccgg cgggagagcg tggtgcaccg     180
ggtgaacgcg gtgcaccggg atttcgtggt ccagcaggac cgaatggtat ccctggtgaa     240
aaaggaccgg caggtgagcg tggagcgcca ggtgaacgtg gcgcaccggg ttttcgtgga     300
ccggcaggcc cgaatggtat tccgggtgaa aaaggcccgg caggtgaacg tggtgccccg     360
ggtgaacgtg gtgcgcctgg atttcgtggc ccggcaggac cgaacggtat ccctggagaa     420
aaaggtcctg caggtgagcg cggtgcgccg ggcgagcgtg gtgcccctgg ttttcgcggt     480
ccggcaggcc ctaatggtat tcctggagaa aaaggccctg caggtgaacg cggagcaccg     540
ggtgagcgtg gcgcacctgg ttttcgtggt cctgcaggcc cgaacggtat tccgggcgaa     600
aaaggtccag caggtgaacg tggtgctccg ggtgaacgtg gtgcacctgg atttcgcggt     660
cctgctggtc cgaatggtat tccaggtgaa aaaggtccgg caggagagcg tggagcaccg     720
ggagaacgtg gtgcaccggg ctttcgtggt ccggccggtc ctaacggtat cccaggtgaa     780
aaaggtccgg ccggcgagcg tggcgcccct ggtgagcgtg gtgctcctgg ttttcgtggt     840
ccggctggtc cgaacggaat tcctggtgag aaaggtccgg ctggcgaacg tggtgcaccg     900
ggtgaacgtg gtgcaccggg tttccgtggt ccgcgggtc ctaatggtat cccgggtgaa     960
aaaggtccgg caggtgaacg tggtgcaccg ggtgaacgtg gtgcaccggg tttcgcgga    1020 ccggcaggac ctaatggtat tccgggagaa aaaggacctg cgggtgaacg tggtgcaccg    1080

-continued

```
ggtgaacgtg gtgcaccggg ttttcgtggt ccggcaggtc ctaatggaat tcctggagag   1140
aaaggacctg caggtgaacg tggtgcaccg ggtgaacgtg gtgcaccggg ttttcgtggt   1200
ccggcaggtc caaatggtat tccgggtgaa aaggtccgg caggtgaacg tggtgcaccg    1260
ggtgaacgtg gtgcaccggg ttttcgtggt ccggcaggtc cgaatggcat tcctggtgaa   1320
aaaggtccgg caggtgaacg tggtgcaccg ggtgaacgtg gtgcaccggg ttttcgtggt   1380
ccggcaggtc cgaatggtat tccgggtgaa aaggtccgg caggtgaacg tggtgcaccg    1440
ggcccgcctg gtccttgttg tggcggcggc                                    1470
```

<210> SEQ ID NO 11
<211> LENGTH: 486
<212> TYPE: PRT
<213> ORGANISM: artifical sequence
<220> FEATURE:
<223> OTHER INFORMATION: T16b

<400> SEQUENCE: 11

```
Gly Glu Arg Gly Ala Pro Gly Phe Arg Gly Pro Ala Gly Pro Asn Gly
1               5                   10                  15

Ile Pro Gly Glu Lys Gly Pro Ala Gly Glu Arg Gly Ala Pro Gly Glu
            20                  25                  30

Arg Gly Ala Pro Gly Phe Arg Gly Pro Ala Gly Pro Asn Gly Ile Pro
        35                  40                  45

Gly Glu Lys Gly Pro Ala Gly Glu Arg Gly Ala Pro Gly Glu Arg Gly
    50                  55                  60

Ala Pro Gly Phe Arg Gly Pro Ala Gly Pro Asn Gly Ile Pro Gly Glu
65                  70                  75                  80

Lys Gly Pro Ala Gly Glu Arg Gly Ala Pro Gly Glu Arg Gly Ala Pro
                85                  90                  95

Gly Phe Arg Gly Pro Ala Gly Pro Asn Gly Ile Pro Gly Glu Lys Gly
            100                 105                 110

Pro Ala Gly Glu Arg Gly Ala Pro Arg Ser Gly Glu Arg Gly Ala Pro
        115                 120                 125

Gly Phe Arg Gly Pro Ala Gly Pro Asn Gly Ile Pro Gly Glu Lys Gly
    130                 135                 140

Pro Ala Gly Glu Arg Gly Ala Pro Gly Glu Arg Gly Ala Pro Gly Phe
145                 150                 155                 160

Arg Gly Pro Ala Gly Pro Asn Gly Ile Pro Gly Glu Lys Gly Pro Ala
                165                 170                 175

Gly Glu Arg Gly Ala Pro Gly Glu Arg Gly Ala Pro Gly Phe Arg Gly
            180                 185                 190

Pro Ala Gly Pro Asn Gly Ile Pro Gly Glu Lys Gly Pro Ala Gly Glu
        195                 200                 205

Arg Gly Ala Pro Gly Glu Arg Gly Ala Pro Gly Phe Arg Gly Pro Ala
    210                 215                 220

Gly Pro Asn Gly Ile Pro Gly Glu Lys Gly Pro Ala Gly Glu Arg Gly
225                 230                 235                 240

Ala Pro Arg Ser Gly Glu Arg Gly Ala Pro Gly Phe Arg Gly Pro Ala
                245                 250                 255

Gly Pro Asn Gly Ile Pro Gly Glu Lys Gly Pro Ala Gly Glu Arg Gly
            260                 265                 270

Ala Pro Gly Glu Arg Gly Ala Pro Gly Phe Arg Gly Pro Ala Gly Pro
        275                 280                 285
```

Asn Gly Ile Pro Gly Glu Lys Gly Pro Ala Gly Glu Arg Gly Ala Pro
            290                 295                 300
Gly Glu Arg Gly Ala Pro Gly Phe Arg Gly Pro Ala Gly Pro Asn Gly
305                 310                 315                 320
Ile Pro Gly Glu Lys Gly Pro Ala Gly Glu Arg Gly Ala Pro Gly Glu
                325                 330                 335
Arg Gly Ala Pro Gly Phe Arg Gly Pro Ala Gly Pro Asn Gly Ile Pro
            340                 345                 350
Gly Glu Lys Gly Pro Ala Gly Glu Arg Gly Ala Pro Arg Ser Gly Glu
        355                 360                 365
Arg Gly Ala Pro Gly Phe Arg Gly Pro Ala Gly Pro Asn Gly Ile Pro
370                 375                 380
Gly Glu Lys Gly Pro Ala Gly Glu Arg Gly Ala Pro Gly Glu Arg Gly
385                 390                 395                 400
Ala Pro Gly Phe Arg Gly Pro Ala Gly Pro Asn Gly Ile Pro Gly Glu
                405                 410                 415
Lys Gly Pro Ala Gly Glu Arg Gly Ala Pro Gly Glu Arg Gly Ala Pro
            420                 425                 430
Gly Phe Arg Gly Pro Ala Gly Pro Asn Gly Ile Pro Gly Glu Lys Gly
        435                 440                 445
Pro Ala Gly Glu Arg Gly Ala Pro Gly Glu Arg Gly Ala Pro Gly Phe
450                 455                 460
Arg Gly Pro Ala Gly Pro Asn Gly Ile Pro Gly Glu Lys Gly Pro Ala
465                 470                 475                 480
Gly Glu Arg Gly Ala Pro
                485

<210> SEQ ID NO 12
<211> LENGTH: 1458
<212> TYPE: DNA
<213> ORGANISM: artifical sequence
<220> FEATURE:
<223> OTHER INFORMATION: T16b

<400> SEQUENCE: 12
ggcgagcgtg gtgcacctgg ttttcgtggc cctgcaggcc cgaatggcat cccgggtgaa      60
aaaggcccgg caggcgaacg tggcgcccct ggtgaacgcg cgcacctgg tttccgtggc      120 ccggcaggtc ctaacggtat cccgggcgaa aagggtcctg caggcgagcg tggcgccccg     180
ggtgaacgcg gtgcccctgg ctttcgcggt cctgccggcc taacggcat tccgggtgag     240 aaaggtcctg ccggtgagcg cggtgcccct ggtgagcgcg cgcaccggg ctttcgtggc      300 ccggccggtc ctaatggtat tcctggcgag aagggtccgg caggtgaacg cggtgcacct    360
agatccggcg agcgtggtgc acctggtttt cgtggccctg caggcccgaa tggcatcccg     420
ggtgaaaaag gcccggcagg cgaacgtggc gccctggtg aacgcggcgc acctggtttc      480
cgtggcccgg caggtcctaa cggtatcccg ggcgaaaagg gtcctgcagg cgagcgtggc     540
gccccgggtg aacgcggtgc ccctggcttt cgcggtcctg ccggccctaa cggcattccg    600
ggtgagaaag gtcctgccgg tgagcgcggt gcccctggtg agcgcggcgc accgggcttt    660
cgtggcccgg ccggtcctaa tggtattcct ggcgagaagg gtccggcagg tgaacgcggt    720
gcacctagat ccggcgagcg tggtgcacct ggttttcgtg gccctgcagg cccgaatggc    780
atcccgggta aaaaggccc ggcaggcgaa cgtggcgccc tggtgaacg cggcgcacct     840 ggtttccgtg gcccggcagg tcctaacggt atcccgggcg aaaagggtcc tgcaggcgag    900

```
cgtggcgccc cgggtgaacg cggtgcccct ggctttcgcg gtcctgccgg ccctaacggc     960
attccgggtg agaaaggtcc tgccggtgag cgcggtgccc ctggtgagcg cggcgcaccg    1020
ggctttcgtg gcccggccgg tcctaatggt attcctggcg agaagggtcc ggcaggtgaa    1080
cgcggtgcac ctagatccgg cgagcgtggt gcacctggtt ttcgtggccc tgcaggcccg    1140
aatggcatcc cgggtgaaaa aggcccggca ggcgaacgtg gcgcccctgg tgaacgcggc    1200
gcacctggtt tccgtggccc ggcaggtcct aacggtatcc cgggcgaaaa gggtcctgca    1260
ggcgagcgtg gcgccccggg tgaacgcggt gcccctggct ttcgcggtcc tgccggccct    1320
aacggcattc cgggtgagaa aggtcctgcc ggtgagcgcg gtgcccctgg tgagcgcggc    1380
gcaccgggct ttcgtggccc ggccggtcct aatggtattc ctggcgagaa gggtccggca    1440
ggtgaacgcg gtgcacct                                                  1458
```

<210> SEQ ID NO 13
<211> LENGTH: 23
<212> TYPE: PRT
<213> ORGANISM: Artificial Sequence
<220> FEATURE:
<223> OTHER INFORMATION: Human type III collagen

<400> SEQUENCE: 13

```
Pro Gly Phe Arg Gly Pro Ala Gly Pro Asn Gly Ile Pro Gly Glu Lys
1               5                   10                  15

Gly Pro Ala Gly Glu Arg Gly
            20
```

POLYPEPTIDE, PROCESS FOR THE PRODUCTION THEREOF AND USE THEREOF

REFERENCE TO RELATED APPLICATION

This application claims foreign priority to Chinese Patent Application No. 201811438582.6, filed on Nov. 28, 2018, the entire contents of which is incorporated herein by reference.

SEQUENCE LISTING

This application contains a Sequence Listing which has been submitted electronically in ASCII format and is hereby incorporated by reference. The ASCII text file, created Jan. 25, 2022, named Updated_Seq_Listing_131064_00601.txt, and is 30,868 bytes in size.

TECHNICAL FIELD

The invention belongs to the technical field of genetic engineering, and relates to a polypeptide, a process for the production thereof, and a use thereof.

BACKGROUND

Collagen is a type of protein widely distributed in connective tissues of the human body, and is also the most abundant protein in the human body and can account for 25% to 35% of total proteins. Its main function is to maintain the extracellular environment, maintain the normal physiological functions of tissues and organs, and repair the body damage. Collagen is a natural biological resource, which has the biological histocompatibility, support elasticity to cells and degradability that other polymer materials cannot achieve. Therefore, collagen may be widely used in industries such as medicine and cosmetics.

However, natural collagen is insoluble in water and is not uniform in nature, and therefore it is difficult to be utilized by the human body and often needs to be treated by chemical means. Moreover, all the collagen products currently available on the market are taken from tissues of animals such as pigs, cattle and fish, and it is difficult to avoid viral infection, which, together with their incompatibility with the human body, may lead to immune rejection and allergy symptoms. If collagen is extracted from human placenta raw materials, it not only has a limited source, but also faces severe punishment from the law. Therefore, the current collagen can only be used in cosmetics and health care products, and the original biological function of collagen cannot be exerted at all.

Structurally, the structure of the natural collagen of the human body is very complicated, resulting in that it is very difficult to express and mass-produce human collagen by conventional means. The natural collagen molecule has a special supercoiled structure consisting of three polypeptide chains which have no intrachain hydrogen bonds and are supported only by interchain hydrogen bonds. This helical structure is a left-handed helix with three amino acid residues as the basic repeat, and these three amino acid residues are typically Gly-X-Pro. Gly is essential for the formation of hydrogen bonds in collagen; it has no side chains itself, resulting in that collagen piles up tightly. At a higher structural level, collagen supercoils will further associate to form collagen fibrils. In organisms, the synthesis and modification of collagen begins with procollagen and undergoes many chemical changes such as hydroxylation, glycosylation, and cross-linking, and are regulated by a variety of biological enzymes. In addition to the collagen chain, procollagen also contains spherical heads and tails. Without these heads and tails, the collagen chain would not fold into the correct triple helix, leading to loss of the biological activity of collagen. Therefore, collagen prepared according to the original gene sequence is unlikely to spontaneously organize in vitro to form the correct spatial structure. Such difficulties have seriously hindered the development and production of human collagen.

The traditional process for the production of collagen is to treat animal-derived tissues by acid, alkali, and enzymolysis methods and extract collagen derivatives. The collagen extracted by these methods has lost the original biological activity and thus cannot be applied to the biomedical field to perform the true function. With the development of modern biotechnology, people continue to try to utilize transgenic techniques to prepare recombinant human collagen in animal, plant and microbial expression systems, which solves many shortcomings of the traditional extraction processes. Foreign research institutes have obtained milk comprising human collagen by cultivating mice containing a human collagen gene, whereas the cost of such production is too high and the production cycle is too long, so that it cannot be put into mass production.

Chinese Patent Invention No. 201210482543.2 discloses a recombinant human collagen and a process for producing the same, and it discloses a recombinant human collagen obtained by linking a type III collagen peptide segment via a linker and adding a stable sequence at C-terminus.

However, there is a need in the art for more recombinant human collagens with better characteristics.

SUMMARY

The present invention provides the following contents:

1. A polypeptide comprising n repeats of a sequence set forth in SEQ ID No. 1, n being an integer greater than or equal to 1, preferably 1, 2, 3, 4, 5, 6, 7, 8, 9, 10, 12, 14, 16, 20, 24, or 32, wherein when n is an integer greater than or equal to 2, the repeats of the sequence are directly linked.

2. The polypeptide according to item 1, wherein the polypeptide comprises a sequence set forth in SEQ ID No. 2 or does not comprise a sequence set forth in SEQ ID No. 2.

3. The polypeptide according to item 1 or 2, wherein the polypeptide comprises:

a) an amino acid sequence of SEQ ID No. 3;

b) an amino acid sequence having 90%, 92%, 95%, 96%, 97%, 98% or 99% identity to the amino acid sequence of SEQ ID No. 3 and retaining cell adhesion effect of the amino acid sequence of SEQ ID No. 3;

c) an amino acid sequence in which one or more amino acid residues are added, substituted, deleted or inserted in the amino acid sequence of SEQ ID No. 3 and retaining cell adhesion effect of the amino acid sequence of SEQ ID No. 3; or d) an amino acid sequence encoded by a nucleotide sequence which hybridizes under stringent conditions to a polynucleotide sequence encoding the amino acid sequence of SEQ ID No. 3, the amino acid sequence retaining cell adhesion effect of the amino acid sequence of SEQ ID No. 3, and the stringent conditions being medium stringency conditions, medium-high stringency conditions, high stringency conditions, or very high stringency conditions.

4. A polynucleotide encoding the polypeptide according to any of items 1-3.

5. An expression vector comprising the polynucleotide according to item 4, and optionally comprising a nucleic acid sequence encoding SEQ ID No. 4, wherein the nucleic acid sequence encoding SEQ ID No. 4 is directly linked to the 5' end of the coding nucleic acid sequence of the polypeptide, preferably the expression vector comprises the nucleic acid sequence of SEQ ID No. 5.

6. A host cell comprising the expression vector according to item 5, wherein the host cell is preferably *Escherichia coli*.

7. A process for the production of the polypeptide according to item 1, comprising:

(1) cultivating the host cell according to item 6 in a production medium and producing the polypeptide;

(2) harvesting the polypeptide, and optionally digesting the polypeptide, preferably digesting the polypeptide with TEV protease; and (3) purifying the polypeptide by a Ni column and/or an anion exchange chromatography;

wherein optionally the process for the production does not include an additional step of removing endotoxin; wherein preferably the purified polypeptide is substantially free of endotoxin or contains less than 5 EU/ml endotoxin.

8. A composition comprising the polypeptide according to item 1, wherein the composition is preferably a medical device, a tissue engineering product, a cosmetic or a health care product, preferably the polypeptide is in the form of an aqueous solution of the polypeptide, preferably the composition is free of a component that prevents degradation of the polypeptide, and preferably the composition is a composition for long-term use, the long-term use being preferably more than half a year of use.

9. Use of the polypeptide according to item 1 in the manufacture of a composition, preferably a medical device, a tissue engineering product, a cosmetic, or a health supplement, wherein preferably the polypeptide is in the form of an aqueous solution of the polypeptide, preferably the composition is free of a component that prevents degradation of a polypeptide, and the composition is a composition for long-term use, the long-term use being more than half a year of use.

10. Use of the polypeptide according to item 1 for promoting cell adhesion.

11. Use of an amino acid sequence of SEQ ID No. 4 or the expression vector according to the present invention for the production of the polypeptide according to the present invention.

The polypeptide of the present invention has the following advantages: its cell adhesion is stronger than the existing recombinant type III collagens; it has higher stability in an aqueous solution, as demonstrated by degradation in more than half a year, thus eliminating the need to add a reagent for prevent polypeptide degradation; most of the endotoxin may be removed by purification by a Ni column and an anion exchange chromatography from the product of the polypeptide, and the purified polypeptide product is substantially free of endotoxin or contains 5 EU/ml or less endotoxin; the polypeptide of the present invention is obtained from a host cell in higher yield and purity.

DETAILED DESCRIPTION

Figure 1:
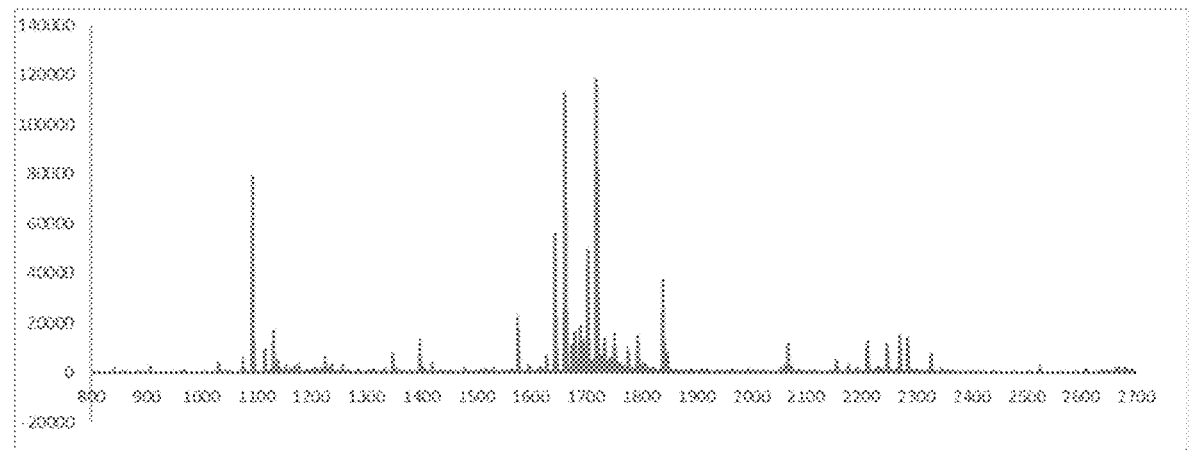
FIG. 1: Mass spectrometry peak results of the expressed product.

Further description is provided below to facilitate an understanding of the invention.

As used herein, "medical instrument" refers to apparatus, devices, appliances, in vitro diagnostic reagents and calibrators, materials, and other similar or related articles that are used directly or indirectly in the human body.

As used herein, "tissue engineering product" refers to a product used in tissue engineering. Tissue engineering is an emerging discipline that combines cell biology and materials science to construct tissues or organs in vitro or in vivo.

The present invention is based, in part, on the following findings by the inventors: when a polypeptide comprising a plurality of repeat sequences of SEQ ID No. 1 is expressed in *E. coli*, in order to increase the gelling property of the recombinantly expressed polypeptide, it is often necessary to add a sequence such as the hinge-region amino acids GPPGPCCGGG (SEQ ID No. 2) at the C-terminus of the polypeptide to aid gelling (Reference: Journal of Biochemistry. 2004; 136: 643-649) because the protein of interest is a truncated protein and lacks the hinge protein structure of the full-length protein. Therefore, a polypeptide sequence comprising SEQ ID NO. 3 and SEQ ID No. 2, for example, the sequence T16a of SEQ ID No. 9, was designed; however, it was found that when the polypeptide of the sequence such as T16a was cultured in a shake flask or a fermentation tank, most of the polypeptide of interest formed a gelatinous precipitate which could not be dissolved and purified, so the yield was very low. Previously, in order to settle this problem, through addition of non-collagen amino acid linkers between the repeat sequences (SEQ ID No. 1), a polypeptide comprising a plurality of such repeat sequences was obtained; besides, the modification of such a polypeptide was also mainly concentrated on the linker amino acid residues and C-terminal hinge region amino acids, also known as a C-terminal stable sequence.

Surprisingly, after analyzing the crystal structure of SEQ ID No. 1, the inventors found that the region of SEQ ID No. 1 can form a very stable collagen trimer structure without the involvement of a hinge region. Therefore, the inventors continued to modify the polypeptide sequence and found that in the process of expressing a polypeptide of the sequence set forth in SEQ ID No. 5, which comprises the sequence set forth in SEQ ID No. 4 and the sequence set forth in SEQ ID No. 3, a polypeptide comprising the sequence set forth in SEQ ID No. 3 may be obtained in large quantities, and the involvement of the C-terminal stable sequence is no further required. Moreover, at this time, a polypeptide does not form a colloidal structure prematurely while being recombinantly expressed, thereby not affecting subsequent protein purification. Furthermore, the inventors have surprisingly found that compared with the recombinant human collagen (SEQ ID No. 6) in Chinese Patent Invention No. 201210482543.2, the polypeptide of the present invention is more stable in aqueous solution, may be obtained from host cells in higher yield and purity, and has significantly lower endotoxin after purification by a Ni column and an anion exchange column.

(SEQ ID NO. 6)
GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPRSGERGAPGFRGPAGPNGIPGEKGPAGERG

APGERGAPGFRGPAGPNGIPGEKGPAGERGAPGERGAPGFRGPAGPNGIP

GEKGPAGERGAPGERGAPGFRGPAGPNGIPGEKGPAGERGAPRSGERGAP

GFRGPAGPNGIPGEKGPAGERGAPGERGAPGFRGPAGPNGIPGEKGPAGE

RGAPGERGAPGFRGPAGPNGIPGEKGPAGERGAPGERGAPGFRGPAGPNG

NGIPGEKGPAGERGAPRSGERGAPGFRGPAGPNGIPGEKGPAGERGAPGE

RGAPGFRGPAGPNGIPGEKGPAGERGAPGERGAPGFRGPAGPNGIPGEKG

PAGERGAPGERGAPGFRGPAGPNGIPGEKGPAGERGAPRSPEFGPPGPCC

GGG.

In the present invention, the used repeat sequence of SEQ ID No. 1 is GERGAPGFRGPAGPNGIPGEKGPAGERGAP (SEQ ID No. 1). The polypeptide of the present invention may comprise a plurality of repeat sequences set forth in SEQ ID No. 1, provided that there is no linker between the repeat sequences. Herein, the linker may be one or more amino acid residues. The present invention does not limit the number of repeat sequences as long as it can actualize the characteristics verified in the adhesion examples. Preferably, the number of repeat sequences is 16, i.e., a polypeptide comprising the sequence set forth in SEQ ID No. 3:

(SEQ ID No. 3)
GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPGERGAPGFRGPAGPNGIPGEKGPAGERGAP

GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPGERGAPGFRGPAGPNGIPGEKGPAGERGAP

GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPGERGAPGFRGPAGPNGIPGEKGPAGERGAP

GERGAPGFRGPAGPNGIPGEKGPAGERGAP

The polypeptide sequence of the invention may comprise the C-terminal sequence GPPGPCCGGG (SEQ ID No. 2). When expressing a polypeptide comprising a plurality of repeat sequences, those skilled in the art typically consider adding said sequence to increase the stability of the expressed polypeptide. Preferably, the polypeptide sequence may not comprise the C-terminal sequence GPPGPCCGGG (SEQ ID No. 2), maintaining sequence identity to human type III collagen without introducing additional amino acids.

When the polypeptide sequence of the present invention is expressed, the sequence of ENLYFQ (SEQ ID No. 4) should be added at its N-terminus, which can be cut by TEV protease to directly obtain the sequence of SEQ ID No. 3. Preferably, the ENLYFQ (SEQ ID No. 4) sequence is directly linked to the N-terminus, to get the sequence of SEQ ID No. 5:

(SEQ ID NO. 5)
ENLYFQGERGAPGFRGPAGPNGIPGEKGPAGERGAPGERGAPGFRGPAGP

NGIPGEKGPAGERGAPGERGAPGFRGPAGPNGIPGEKGPAGERGAPGERG

APGFRGPAGPNGIPGEKGPAGERGAPGERGAPGFRGPAGPNGIPGEKGPA

GERGAPGERGAPGFRGPAGPNGIPGEKGPAGERGAPGERGAPGFRGPAGP

NGIPGEKGPAGERGAPGERGAPGFRGPAGPNGIPGEKGPAGERGAPGERG

APGFRGPAGPNGIPGEKGPAGERGAPGERGAPGFRGPAGPNGIPGEKGPA

GERGAPGERGAPGFRGPAGPNGIPGEKGPAGERGAPGERGAPGFRGPAGP

NGIPGEKGPAGERGAPGERGAPGFRGPAGPNGIPGEKGPAGERGAPGERG

APGFRGPAGPNGIPGEKGPAGERGAPGERGAPGFRGPAGPNGIPGEKGPA

GERGAPGERGAPGFRGPAGPNGIPGEKGPAGERGAP.

In the present invention, polypeptides are recombinant type III collagens, which are used interchangeably herein with recombinant human collagens.

In the present invention, recombination of human collagens may be carried out by a conventional method in the art. For example, they may be produced as follows: (1) construction of E. coli genetically engineered bacteria; (2) fermentation culture of E. coli genetically engineered bacteria; (3) induction and expression of recombinant human collagen; and (4) purification and optional digestion of recombinant human collagen.

In step (1), the construction of E. coli genetically engineered bacteria may be carried out as follows: (1) obtaining a gene fragment of interest; (2) inserting the obtained gene fragment of interest into PET-32a expression vector to obtain a recombinant expression plasmid; (3) transforming the recombinant expression plasmid into E. coli competent cell BL21 (DE3), and screening positive E. coli genetically engineered bacteria.

In steps (2) and (3), the fermentation culture of E. coli genetically engineered bacteria and the induction and expression of recombinant human collagen may be carried out as follows: (1) picking up optimum single colonies of E. coli genetically engineered bacteria from LAB plate, placing in 10 mL of LB medium, and culturing at 37° C. and 220 rpm for 12-16 hours; (2) inoculating bacterial solution into 2×YT medium at 1:100 for scale-up culture, and culturing at 37° C. for about 3 hours, and when $OD_{600}$ is between 0.4 and 0.6, adding IPTG to a final concentration of 0.5 mM for induction, continuing to culture at 16° C. for 20 hours, and collecting bacteria by centrifugation.

In step (4), the purification and digestion of recombinant human collagen polypeptide may be carried out as follows: (1) resuspending the bacteria with phosphate buffer (40 mM $NaH_2PO_3$, 500 mM NaCl, pH 7.8) prior to ultrasonication, and collecting the supernatant by centrifugation; (2) using NI-NTA affinity column to bind to recombinant human collagen, and after washing out impurity proteins with 10 mM imidazole, adding TEV protease, performing on-column enzymatic digestion at 4° C. for 16 hours, and finally obtaining the collagen polypeptide of interest.

The host cell may be a eukaryotic cell, such as a fungus and yeast, a prokaryotic cell, such as an Enterobacteriaceae bacterium. It will be appreciated that those skilled in the art can replace the above-mentioned *E. coli* strain with other expression strains as a host cell.

The present invention further provides a nucleic acid molecule comprising a nucleic acid sequence encoding a polypeptide of the present invention. The nucleic acid may be DNA or cDNA. The nucleic acid molecule may consist essentially of a nucleic acid sequence encoding the peptide of the present invention, or may consist solely of a nucleic acid sequence encoding the peptide of the present invention. Such a nucleic acid molecule may be synthesized by methods known in the art. Due to the degeneracy of genetic code, those skilled in the art will appreciate that nucleic acid molecules of different nucleic acid sequences may encode the same amino acid sequence.

The present invention further provides a vector comprising the nucleic acid sequence of the present invention. Suitable vectors are known in the field of vector construction, including choices of promoters and other regulatory elements, such as enhancer elements. The vector of the present invention comprises a sequence suitable for introduction into a cell. For example, the vector may be an expression vector; in the vector, the coding sequence of the polypeptide is under the control of its own cis-acting regulatory element, and the design of the vector facilitates gene integration or gene replacement in a host cell.

Those skilled in the art will appreciate that in the present invention, the term "vector" includes a DNA molecule, for example, a plasmid, a phage, virus or other vectors; it comprises one or more heterologous or recombinant nucleic acid sequences. Suitable phages and viral vectors include, but are not limited to, lambda-phage, EMBL phage, simian virus, bovine papilloma virus, Epstein-Barr virus, adenovirus, herpes virus, murine sarcoma virus, murine mammary tumor virus, lentivirus, and the like.

The polypeptide of the present invention comprises a sequence set forth in SEQ ID No. 3 or a sequence in which one or more amino acids are substituted, deleted, inserted and/or added in the sequence set forth in SEQ ID No. 3, as long as the polypeptide of the present invention retains cell adhesion effect of the amino acid sequence of SEQ ID No. 3. "More" may be 2, 3, 4, 5, 6, 7, 8, 9, 10 or 11.

Amino acid addition refers to addition of an amino acid(s) at the C-terminus or the N-terminus of an amino acid sequence, e.g. SEQ ID No. 3, as long as the polypeptide of the present invention retains cell adhesion effect of the amino acid sequence of SEQ ID No. 3.

Amino acid substitution refers to replacement of an amino acid residue at a position in an amino acid sequence, e.g. the sequence of SEQ ID No. 3, with another amino acid residue, as long as the polypeptide of the present invention retains cell adhesion effect of the amino acid sequence of SEQ ID No. 3.

Amino acid insertion refers to insertion of an amino acid residue(s) at an appropriate position(s) in an amino acid sequence, e.g. the sequence of SEQ ID No. 3, and all or part of the inserted amino acid residues may also be adjacent to each other, or the inserted amino acid residues are not adjacent to each other, as long as the polypeptide of the present invention retains cell adhesion effect of the amino acid sequence of SEQ ID No. 3. The positions of the inserted amino acid herein are not between repeat sequences.

Amino acid deletion means that 1, 2, 3 or more amino acids may be deleted from an amino acid sequence, e.g. the sequence of SEQ ID No. 3, as long as the polypeptide of the present invention retains cell adhesion effect of the amino acid sequence of SEQ ID No. 3.

In the present invention, the substitution may be a conservative amino acid substitution, meaning that 3, more preferably 2 or 1 amino acid is replaced by an amino acid having similar or same property to form a peptide compared to the amino acid sequence of SEQ ID No. 3. These conservative variant peptides may be produced by amino acid replacements according to Table 1.

| Initial residue | Representative substitution | Preferred substitution |
|---|---|---|
| Ala (A) | Val:Leu:Ile | Val |
| Arg (R) | Lys:Gln:Asn | Lys |
| Asn (N) | Gln:His:Lys:Arg | Gln |
| Asp (D) | Glu | Glu |
| Cys (C) | Ser | Ser |
| Gln (Q) | Asn | Asn |
| Glu (E) | Asp | Asp |
| Gly (G) | Pro:Ala | Ala |
| His (H) | Asn:Gln:Lys:Arg | Arg |
| Ile (I) | Leu:Val:Met:Ala:Phe | Leu |
| Leu (L) | Ile:Val:Met:Ala:Phe | Ile |
| Lys (K) | Arg:Gln:Asn | Arg |
| Met (M) | Leu:Phe:Ile | Leu |
| Phe (F) | Leu:Val:Ile:Ala:Tyr | Leu |
| Pro (P) | Ala | Ala |
| Ser (S) | Thr | Thr |
| Thr (T) | Ser | Ser |
| Trp (W) | Tyr:Phe | Tyr |
| Tyr (Y) | Trp:Phe:Thr:Ser | Phe |
| Val (V) | Ile:Leu:Met:Phe:Ala | Leu |

As used herein, the terms "medium stringency conditions", "medium-high stringency conditions", "high stringency conditions" or "very high stringency conditions" describe conditions for nucleic acid hybridization and washing. Guidance for performing hybridization reactions is described in Current Protocols in Molecular Biology, John Wiley & Sons, N.Y. (1989), 6.3.1-6.3.6, which is incorporated herein by reference. Both a method involving water and a method not involving water are described in this reference, and any of them may be used. For example, specific hybridization conditions are as follows: (1) low stringency hybridization conditions are hybridization in 6× sodium chloride/sodium citrate (SSC) at about 45° C., followed by two washes in 0.2×SSC, 0.1% SDS at at least 50° C. (for low stringency hybridization conditions, wash temperature can be raised to 55° C.); (2) medium stringency conditions are hybridization in 6×SSC at about 45° C., followed by one or more washes in 0.2×SSC, 0.1% SDS at 60° C.; (3) high stringency conditions are hybridization in 6×SSC at about 45° C., followed by one or more washes in 0.2×SSC, 0.1% SDS at 65° C.; and preferably (4) very high stringency conditions are 0.5 M sodium phosphate, 7% SDS, followed by one or more washes in 0.2×SSC, 1% SDS at 65° C., then at 65° C.

EXAMPLES

The following examples are provided to illustrate the invention. Those skilled in the art will appreciate that the examples are merely illustrative but not restrictive. The present invention is only limited by the scope of the appended claims.

Example 1: Construction and Expression of Recombinant Human Collagen Polypeptides Construction and Expression of TE16C Gene Expression Vector 1. The full-length protein sequence of human collagen TE16C used in Example 1 is the sequence set forth in SEQ ID No. 5 and has a full length of 486 aa, and its corresponding gene has a full length of 1458 bp. After codon optimization for the codon of *E. coli* (nucleotide sequence:

```
gaaaacctgtataccagggtgaacgtggtgcaccaggattcgtggtccgg caggtccgaatggaattccgggtgagaaaggaccggctggtgagcgtggt gcgccgggtgaacgtggagcgcctggttttcgtggcccagcaggtccgaa cggtattcctggtgaaaaaggtccggcgggagagcgtggtgcaccgggtg aacgcggtgcaccgggatttcgtggtccagcaggaccgaatggtatccct ggtgaaaaaggaccggcaggtgagcgtggagcgcaggtgaacgtggcgc accgggttttcgtggaccggcaggcccgaatggtattccgggtgaaaaag gcccggcaggtgaacgtggtgcccggtgaacgtggtgcgcctggattt cgtggcccggcaggaccgaacggtatccctggagaaaaaggtcctgcagg tgagcgcggtgcgccgggcgagcgtggtgccctggattcgcggtccggc aggccctaatggtattcctggagaaaaaggccctgcaggtgaacgcggag caccgggtgagcgtggcgcacctggttttcgtggtcctgcaggcccgaac ggtattccgggcgaaaaaggtccagcaggtgaacgtggtgctccgggtga acgtggtgcacctggatttcgcggtcctgctggtccgaatggtattccag gtgaaaaaggtccggcaggagagcgtggagcaccgggagaacgtggtgca ccgggattcgtggtccggccggtcctaacggtatcccaggtgaaaaaggt ccggccggcgagcgtggcgcccctggtgagcgtggtgctcctggattcgt ggtccggctggtccgaacggaattcctggtgagaaaggtccggctggcga acgtggtgcaccgggtgaacgtggtgcaccgggtttccgtggtccggcgg gtcctaatggtatcccgggtgaaaaaggtccggcaggtgaacgtggtgca ccgggtgaacgtggtgcaccgggattcgcggaccggcaggacctaatggt attccgggagaaaaaggacctgcgggtgaacgtggtgcaccgggtgaacg tggtgcaccgggattcgtggtccggcaggtcctaatggaattcctggaga gaaaggacctgcaggtgaacgtggtgcaccgggtgaacgtggtgcaccgg gttttcgtggtccggcaggtccaaatggtattccgggtgaaaaaggtccg gcaggtgaacgtggtgcaccgggtgaacgtggtgcaccgggttttcgtgg tccggcaggtccgaatggcattcctggtgaaaaaggtccggcaggtgaac gtggtgcaccgggtgaacgtggtgcaccgggttttcgtggtccggcaggt ccgaatggtattccgggtgaaaaaggtccggcaggtgaacgtggtgcacc g, SEQ ID No. 7),
```

Shanghai HuaGen Biotech Co., Ltd. was commissioned to synthesize a gene fragment, and the synthesized TE16C gene fragment was inserted into PET32a expression vector via restriction sites of BamH I (NEB Company, cat. No.: R0136L) and Xho I (NEB Company, Cat. No.: R0146L).

2. The successfully constructed expression plasmid was transformed into *E. coli* competent cell BL21 (DE3) (Merck Company). The specific procedure was as follows: 1: 1 μL of the plasmid was taken and placed into 100 μL of *E. coli* competent cells BL21 (DE3) and allowed to stand on ice for 30 min. 2: This mixture was heat-activated in a 42° C. water bath for 90 s, then quickly placed on ice and allowed to stand for 2 min. 3: 600 μL of non-resistant LB liquid medium was added to the mixture, and cultured at 37° C. and 220 rpm for 1 h. 4: 200 μL of the bacterial solution was uniformly spread onto an LB plate with ampicillin resistance (10 g/L peptone, 5 g/L yeast extract, 10 g/L sodium chloride, 15 g/L agar, and 100 μg/mL ampicillin). 5: The plate was inverted and cultured in a 37° C. incubator, and cultured for about 20 h to grow clear colonies.

3. Monoclonal colonies were picked up from the transformed LB plate and cultured in 10 mL of LB (containing 100 μg/mL ampicillin) medium for 12 h-16 h, then transferred to 2×YT medium (16 g/L peptone, 10 g/L yeast extract, and 5 g/L sodium chloride) at a ratio of 1:100 for scale-up culture, and cultured at 37° C. and 220 rpm until the OD600 of the bacterial solution was between 0.4 and 0.6, and 0.5 mM IPTG (Sigma Company, Cat. No.: 15502-1G) was added to a final concentration of 0.5 mM for induction expression, and induction conditions were culture at 18° C. and 180 rpm for 20 h. Finally, bacteria were collected by centrifugation, and were stored at −20° C. or immediately entered into the next step for purification.

4. (1 L) The bacterial pellets were resuspended in about 50 mL of phosphate buffer (pH 7.8) (40 mM sodium dihydrogen phosphate, 500 mM sodium chloride), then broken by high-pressure bacteria breaking equipment (Scientz Biotechnology Co., LTD.), and centrifuged at 13,000 rpm for 30 min to separate soluble proteins from inclusion bodies.

5. A Ni-NTA (Qiagen Company, Cat. No.: 30210) affinity column was equilibrated with 5 column volumes of binding buffer (40 mM $NaH_2PO_3$, 500 mM NaCl, pH 7.8). Then, the protein supernatant was added to the column and incubated at 4° C. for 0.5-1 h to make the recombinant protein of interest fully bind to the column. Impurity proteins were washed out with 200 mL of washing buffer (10 mM imidazole, 40 mM $NaH_2PO_3$, 500 mM NaCl, pH 7.8) containing 10 mM imidazole (Sigma Company). Finally, an appropriate amount of His-tagged TEV protease (Sigma, SA T4455) was added, and after incubation at 4° C. for 16 h, the flow-through fluid, i.e. the collagen of interest separated from vector protein was collected. The resulting product was dialyzed overnight and lyophilized to dry powder for use.

6. The resulting TE16C protein was measured for purity by SDS-PAGE. The specific procedure was as follows. 40 μL of the purified protein solution was taken, added with 10 μL of 5× protein loading buffer (250 mM Tris-HCl (pH: 6.8), 10% SDS, 0.5% bromophenol blue, 50% glycerol, and 5% β-mercaptoethanol), placed in boiling water at 100° C. and boiled for 10 min. The resulting solution was added to SDS-PAGE protein gel at 10 μL per well, and run at 80 V for 2 h. Then the gel was stained with Coomassie Brilliant Blue staining solution (0.1% Coomassie Brilliant Blue R-250, 25% isopropyl alcohol, and 10% glacial acetic acid) for 20 min, and then decolorized with protein decolorization solution (10% acetic acid, 5% ethanol). Finally, protein activity was measured as compared to a human native collagen.

Construction and Expression of HC16 Gene Expression Vector

1. The full-length protein sequence of human collagen HC16 as a control used in Example 1 is the sequence set forth in SEQ ID No. 6 and has a full length of 501 aa, and its corresponding gene has a full length of 1503 bp. After codon optimization for the codon of *E. coli* (nucleotide sequence:

```
ggcgagcgtggtgcacctggattcgtggccctgcaggcccgaatggcatc ccgggtgaaaaaggcccggcaggcgaacgtggcgcccctggtgaacgcgg cgcacctggtaccgtggcccggcaggtcctaacggtatcccgggcgaaaa gggtcctgcaggcgagcgtggcgcccgggtgaacgcggtgcccctggat tcgcggtcctgccggccctaacggcattccgggtgagaaaggtcctgccg gtgagcgcggtgcccctggtgagcgcggcgcacccgggctttcgtggcccg gccggtcctaatggtattcctggcgagaagggtccggcaggtgaacgcgg tgcacctagatccggcgagcgtggtgcacctggattcgtggccctgcagg cccgaatggcatcccgggtgaaaaaggcccggcaggcgaacgtggcgccc ctggtgaacgcggcgcacctggtttccgtggcccggcaggtcctaacggt atcccgggcgaaaagggtcctgcaggcgagcgtggcgcccgggtgaacg cggtgcccctggattcgcggtcctgccggccctaacggcattccgggtga gaaaggtcctgccggtgagcgcggtgcccctggtgagcgcggcgcaccgg gattcgtggcccggccggtcctaatggtattcctggcgagaagggtccgg caggtgaacgcggtgcacctagatccggcgagcgtggtgcacctggtttt cgtggccctgcaggcccgaatggcatcccgggtgaaaaaggcccggcagg cgaacgtggcgcccctggtgaacgcggcgcacctggtaccgtggcccggc aggtcctaacggtatcccgggcgaaaagggtcctgcaggcgagcgtggcg ccccgggtgaacgcggtgcccctggctttcgcggtcctgccggccctaac ggcattccgggtgagaaaggtcctgccggtgagcgcggtgcccctggtga gcgcggcgcacccgggctttcgtggcccggccggtcctaatggtattcctg gcgagaagggtccggcaggtgaacgcggtgcacctagatccggcgagcgt ggtgcacctggttttcgtggccctgcaggcccgaatggcatcccgggtga aaaaggcccggcaggcgaacgtggcgcccctggtgaacgcggcgcacctg gtaccgtggcccggcaggtcctaacggtatcccgggcgaaaagggtcctg caggcgagcgtggcgccccgggtgaacgcggtgcccctggattcgcggtc ctgccggccctaacggcattccgggtgagaaaggtcctgccggtgagcgc ggtgcccctggtgagcgcggcgcacccggattcgtggcccggccggtcct aatggtattcctggcgagaagggtccggcaggtgaacgcggtgcacctag atctccggaattcggcccgcctggtccttgttgtggcggcggc, SEQ ID No. 8),
```

Shanghai HuaGen Biotech Co., Ltd. was commissioned to synthesize a gene fragment, and the synthesized HC16 gene fragment was inserted into PET32a expression vector via restriction sites of BamH I (NEB Company, Cat. No.: R0136L) and Xho I (NEB Company, Cat. No.: R0146L).

2. The successfully constructed expression plasmid was transformed into *E. coli* competent cell BL21 (DE3) (Merck Company). The specific process is as described above.

3. Monoclonal colonies were picked up from the transformed LB plate and cultured in 10 mL of LB (containing 100 μg/mL ampicillin) medium for 12 h-16 h, then transferred to 2×YT medium (16 g/L peptone, 10 g/L yeast extract, and 5 g/L sodium chloride) at a ratio of 1:100 for scale-up culture, and cultured at 37° C. and 220 rpm until the OD600 of the bacterial solution was between 0.4 and 0.6, and 0.5 mM IPTG (Sigma Company, Cat. No.: 15502-1G) was added to a final concentration of 0.5 mM for induction expression, and induction conditions were culture at 18° C. and 180 rpm for 20 h. Finally, bacteria were collected by centrifugation, and were stored at −20° C. or immediately entered into the next step for purification.

4. (1 L) The bacterial pellets were resuspended in about 50 mL of phosphate buffer (pH 7.8) (40 mM sodium dihydrogen phosphate, 500 mM sodium chloride), then broken by high-pressure bacteria breaking equipment (Scientz Biotechnology Co., LTD.), and centrifuged at 13,000 rpm for 30 min to separate soluble proteins from inclusion bodies.

5. A Ni-NTA (Qiagen Company, Cat. No.: 30210) affinity column was equilibrated with 5 column volumes of binding buffer (40 mM NaH$_2$PO$_3$, 500 mM NaCl, pH 7.8). Then, the protein supernatant was added to the column and incubated at 4° C. for 0.5-1 h to make the recombinant protein of interest fully bind to the column. Impurity proteins were washed out with 200 mL of washing buffer (10 mM imidazole, 40 mM NaH$_2$PO$_3$, 500 mM NaCl, pH 7.8) containing 10 mM imidazole (Sigma Company). Finally, an appropriate amount of His-tagged prescission protease (Ppase, for short) (Sigma, SAE0045) was added, and after incubation at 4° C. for 16 h, the flow-through fluid, i.e. the collagen of interest separated from the vector protein, was collected. The resulting product was dialyzed overnight and lyophilized to dry powder for use.

6. The resulting HC16 protein was measured for purity by SDS-PAGE. The specific procedure was as follows. 40 μL of the purified protein solution was taken, added with 10 μL of 5× protein loading buffer (250 mM Tris-HCl (pH: 6.8), 10% SDS, 0.5% bromophenol blue, 50% glycerol, and 5% β-mercaptoethanol), placed in boiling water at 100° C. and boiled for 10 min. The resulting solution was added to SDS-PAGE protein gel at 10 μL per well, and run at 80 V for 2 h. Then the gel was stained with Coomassie Brilliant Blue staining solution (0.1% Coomassie Brilliant Blue R-250, 25% isopropyl alcohol, and 10% glacial acetic acid) for 20 min, and then decolorized with protein decolorization solution (10% acetic acid, 5% ethanol). Finally, protein activity was measured as compared to a human native collagen. The HC16 protein was verified by the same method as in Chinese Patent Invention 201210482543.2, showing the correct protein size.

Construction and Expression of Polypeptide T16a Containing Repeat Sequences and a C-Terminal Stable Sequence 1. Human collagen T16a used in Example 1, which differs from the TE16C gene or the HC16 gene in that T16a comprises both SEQ ID No. 3 having no linker amino acid and the hinge region amino acid SEQ ID No. 2, has a full length of 490 aa, and its sequence is:

```
                                          (SEQ ID No. 9)
GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPGERGAPGFRGPAGPNGIPGEKGPAGERGAP

GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPGERGAPGFRGPAGPNGIPGEKGPAGERGAP
```

-continued

GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPGERGAPGFRGPAGPNGIPGEKGPAGERGAP

GERGAPGFRGPAGPNGIPGEKGPAGERGAPGPPGPCCGGG

Its corresponding gene has a full length of 1407 bp. After codon optimization for the codon of E. coli (nucleotide sequence:

ggtgaacgtggtgcaccaggttttcgtggtccggcaggtccgaatggaat tccgggtgagaaaggaccggctggtgagcgtggtgcgccgggtgaacgtg gagcgcctggttttcgtggcccagcaggtccgaacggtattcctggtgaa aaaggtccggcgggagagcgtggtgcaccgggtgaacgcggtgcaccggg atttcgtggtccagcaggaccgaatggtatccctggtgaaaaaggaccgg caggtgagcgtggagcgccaggtgaacgtggcgcaccgggattcgtggac cggcaggcccgaatggtattccgggtgaaaaaggcccggcaggtgaacgt ggtgccgcgggtgaacgtggtgcgcctggatttcgtggcccggcaggacc gaacggtatccctggagaaaaaggtcctgcaggtgagcgcggtgcgccgg gcgagcgtggtgcccctggattcgcggtccggcaggccctaatggtattc ctggagaaaaaggccctgcaggtgaacgcggagcaccgggtgagcgtggc gcacctggattcgtggtcctgcaggcccgaacggtattccgggcgaaaaa ggtccagcaggtgaacgtggtgctccgggtgaacgtggtgcacctggatt tcgcggtcctgctggtccgaatggtattccaggtgaaaaggtccggcag gagagcgtggagcacgggagaacgtggtgcaccgggattcgtggtccgg ccggtcctaacggtatcccaggtgaaaaaggtccggccggcgagcgtggc gccctggtgagcgtggtgctcctggttttcgtggtccggctggtccgaa cggaattcctggtgagaaaggtccggctggcgaacgtggtgcaccgggtg aacgtggtgcaccgggtttccgtggtccggcgggtcctaatggtatcccg ggtgaaaaaggtccggcaggtgaacgtggtgcaccgggtgaacgtggtgc accgggttttcgcggaccggcaggaccgtaatggtattccgggagaaaaag gacctgcgggtgaacgtggtgcaccgggtgaacgtggtgcaccgggattc gtggtccggcaggtcctaatggaattcctggagagaaaggacctgcaggt gaacgtggtgcaccgggtgaacgtggtgcaccgggttttcgtggtccggc aggtccaaatggtattccgggtgaaaaaggtccggcaggtgaacgtggtg caccgggtgaacgtggtgcaccgggattcgtggtccggcaggtccgaatg gcattcctggtgaaaaaggtccggcaggtgaacgtggtgcaccgggtgaa cgtggtgcaccgggttttcgtggtccggcaggtccgaatggtattccggg tgaaaaaggtccggcaggtgaacgtggtgcaccgggcccgcctggtcctt gttgtggcggcggc, SEQ ID No. 10), Shanghai HuaGen Biotech Co., Ltd. was commissioned to synthesize a gene fragment, and the synthesized T16a gene fragment was inserted into PET32a expression vector via restriction sites of BamH I (NEB Company, Cat. No.: R0136L) and Xho I (NEB Company, Cat. No.: R0146L).

2. The successfully constructed expression plasmid was transformed into E. coli competent cell BL21 (DE3) (Merck Company). The specific process is as described above.

3. Monoclonal colonies were picked up from the transformed LB plate and cultured in 10 mL of LB (containing 100 µg/mL ampicillin) medium for 12 h-16 h, then transferred to 2×YT medium (16 g/L peptone, 10 g/L yeast extract, and 5 g/L sodium chloride) at a ratio of 1:100 for scale-up culture, and cultured at 37° C. and 220 rpm until the OD600 of the bacterial solution was between 0.4 and 0.6, and 0.5 mM IPTG (Sigma Company, Cat. No.: 15502-1G) was added to a final concentration of 0.5 mM for induction expression, and induction conditions were culture at 18° C. and 180 rpm for 20 h. Finally, bacteria were collected by centrifugation, and were stored at −20° C. or immediately entered into the next step for purification.

4. (1 L) The bacterial pellets were resuspended in about 50 mL of phosphate buffer (pH 7.8) (40 mM sodium dihydrogen phosphate, 500 mM sodium chloride), then broken by high-pressure bacteria breaking equipment (Scientz Biotechnology Co., LTD.), and centrifuged at 13,000 rpm for 30 min to separate soluble proteins from inclusion bodies and collagen colloids.

5. A Ni-NTA (Qiagen Company, Cat. No.: 30210) affinity column was equilibrated with 5 column volumes of binding buffer (40 mM $NaH_2PO_3$, 500 mM NaCl, pH 7.8). Then, the protein supernatant was added to the column and incubated at 4° C. for 0.5-1 h to make the recombinant protein of interest fully bind to the column. Impurity proteins were washed out with 200 mL of washing buffer (10 mM imidazole, 40 mM $NaH_2PO_3$, 500 mM NaCl, pH 7.8) containing 10 mM imidazole (Sigma Company). Finally, an appropriate amount of His-tagged prescission protease (Ppase, for short) (Sigma, SAE0045) was added, and after incubation at 4° C. for 16 h, the flow-through fluid, i.e. the collagen of interest separated from the vector protein was collected. The resulting product was dialyzed overnight and lyophilized to dry powder for use.

6. The resulting T16a protein was measured for purity by SDS-PAGE. The specific procedure was as follows. 40 µL of the purified protein solution was taken, added with 10 µL of 5× protein loading buffer (250 mM Tris-HCl (pH: 6.8), 10% SDS, 0.5% bromophenol blue, 50% glycerol, and 5% β-mercaptoethanol), placed in boiling water at 100° C. and boiled for 10 min. The resulting solution was added to SDS-PAGE protein gel at 10 µL per well, and run at 80 V for 2 h. Then the gel was stained with Coomassie Brilliant Blue staining solution (0.1% Coomassie Brilliant Blue R-250, 25% isopropyl alcohol, and 10% glacial acetic acid) for 20 min, and then decolorized with protein decolorization solution (10% acetic acid, 5% ethanol). Finally, protein activity was measured as compared to a human native collagen.

Construction and Expression of Polypeptide T16b Containing Repeat Sequences and Linker Amino Acids 1. Human collagen T16b used in Example 1, which differs from the TE16C gene or the HC16 gene in that T16b removes the hinge region amino acid SEQ ID No. 2 from the SEQ ID NO. 6 with linker amino acids, has a full length of 486 aa, and its sequence is:

(SEQ ID No. 11)
GERGAPGFRGPAGPNGIPGEKGPAGERGAPGERGAPGFRGPAGPNGIPGE

KGPAGERGAPGERGAPGFRGPAGPNGIPGEKGPAGERGAPGERGAPGFRG

PAGPNGIPGEKGPAGERGAPRSGERGAPGFRGPAGPNGIPGEKGPAGERG

APGERGAPGFRGPAGPNGIPGEKGPAGERGAPGERGAPGFRGPAGPNGIP

GEKGPAGERGAPGERGAPGFRGPAGPNGIPGEKGPAGERGAPRSGERGAP

GFRGPAGPNGIPGEKGPAGERGAPGERGAPGFRGPAGPNGIPGEKGPAGE

RGAPGERGAPGFRGPAGPNGIPGEKGPAGERGAPGERGAPGFRGPAGPNG

IPGEKGPAGERGAPRSGERGAPGFRGPAGPNGIPGEKGPAGERGAPGERG

APGFRGPAGPNGIPGEKGPAGERGAPGERGAPGFRGPAGPNGIPGEKGPA

GERGAPGERGAPGFRGPAGPNGIPGEKGPAGERGAP

Its corresponding gene has a full length of 1458 bp. After codon optimization for the codon of E. coli (nucleotide sequence:

ggcgagcgtggtgcacctggattcgtggccctgcaggcccgaatggcatc ccgggtgaaaaaggcccggcaggcgaacgtggcgcccctggtgaacgcgg cgcacctggtttccgtggcccggcaggtcctaacggtatcccgggcgaaa agggtcctgcaggcgagcgtggcgcccc gggtgaacgcggtgccctggc tttcgcggtcctgccggccctaacggcattccgggtgagaaaggtcctgc cggtgagcgcggtgccctggtgagcgcggcgcaccgggctttcgtggcc cggccggtcctaatggtattcctggcgagaagggtccggcaggtgaacgc ggtgcacctagatccggcgagcgtggtgcacctggttttcgtggccctgc aggcccgaatggcatcccgggtgaaaaaggcccggcaggcgaacgtggcg cccctggtgaacgcggcgcacctggtttccgtggcccggcaggtcctaac ggtatcccgggcgaaaagggtcctgcaggcgagcgtggcgcccc gggtga acgcggtgcccctggctttcgcggtcctgccggccctaacggcattccgg gtgagaaaggtcctgccggtgagcgcggtgccctggtgagcgcggcgca ccgggctttcgtggcccggccggtcctaatggtattcctggcgagaaggg tccggcaggtgaacgcggtgcacctagatccggcgagcgtggtgcacctg gttttcgtggccctgcaggcccgaatggcatcccgggtgaaaaaggcccg gcaggcgaacgtggcgcccctggtgaacgcggcgcacctggtttccgtgg cccggcaggtcctaacggtatcccgggcgaaaagggtcctgcaggcgagc gtggcgcccc gggtgaacgcggtgccctggcttt cgcggtcctgccggccctaacggcattccgggtgagaaaggtcctgccg gtgagcgcggtgccctggtgagcgcggcgcaccgggctttcgtggcccg gccggtcctaatggtattcctggcgagaagggtccggcaggtgaacgcgg tgcacct, SEQ ID No. 12), Shanghai HuaGen Biotech Co., Ltd. was commissioned to synthesize a gene fragment, and the synthesized T16a gene fragment was inserted into PET32a expression vector via restriction sites of BamH I (NEB Company, Cat. No.: R0136L) and Xho I (NEB Company, Cat. No.: R0146L).

2. The successfully constructed expression plasmid was transformed into E. coli competent cell BL21 (DE3) (Merck Company). The specific process is as described above.

3. Monoclonal colonies were picked up from the transformed LB plate and cultured in 10 mL of LB (containing 100 μg/mL ampicillin) medium for 12 h-16 h, then transferred to 2×YT medium (16 g/L peptone, 10 g/L yeast extract, and 5 g/L sodium chloride) at a ratio of 1:100 for scale-up culture, and cultured at 37° C. and 220 rpm until the OD600 of the bacterial solution was between 0.4 and 0.6, and 0.5 mM IPTG (Sigma Company, Cat. No.: 15502-1G) was added to a final concentration of 0.5 mM for induction expression, and induction conditions were culture at 18° C. and 180 rpm for 20 h. Finally, bacteria were collected by centrifugation, and were stored at −20° C. or immediately entered into the next step for purification.

4. (1 L) The bacterial pellets were resuspended in about 50 mL of phosphate buffer (pH 7.8) (40 mM sodium dihydrogen phosphate, 500 mM sodium chloride), then broken by high-pressure bacteria breaking equipment (Scientz Biotechnology Co., LTD.), and centrifuged at 13,000 rpm for 30 min to separate soluble proteins from inclusion bodies.

5. A Ni-NTA (Qiagen Company, Cat. No.: 30210) affinity column was equilibrated with 5 column volumes of binding buffer (40 mM NaH$_2$PO$_3$, 500 mM NaCl, pH 7.8). Then, the protein supernatant was added to the column and incubated at 4° C. for 0.5-1 h to make the recombinant protein of interest fully bind to the column. Impurity proteins were washed out with 200 mL of washing buffer (10 mM imidazole, 40 mM NaH$_2$PO$_3$, 500 mM NaCl, pH 7.8) containing 10 mM imidazole (Sigma Company). Finally, an appropriate amount of His-tagged prescission protease (Ppase, for short) (Sigma, SAE0045) was added, and after incubation at 4° C. for 16 h, the flow-through fluid, i.e. the collagen of interest separated the vector protein was collected. The resulting product was dialyzed overnight and lyophilized to dry powder for use.

6. The resulting T16b protein was measured for purity by SDS-PAGE. The specific procedure was as follows. 40 μL of the purified protein solution was taken, added with 10 μL of 5× protein loading buffer (250 mM Tris-HCl (pH: 6.8), 10% SDS, 0.5% bromophenol blue, 50% glycerol, and 5% β-mercaptoethanol), placed in boiling water at 100° C. and boiled for 10 min. The resulting solution was added to SDS-PAGE protein gel at 10 μL per well, and run at 80 V for 2 h. Then the gel was stained with Coomassie Brilliant Blue staining solution (0.1% Coomassie Brilliant Blue R-250, 25% isopropyl alcohol, and 10% glacial acetic acid) for 20 min, and then decolorized with protein decolorization solution (10% acetic acid, 5% ethanol). Finally, protein activity was measured as compared to a human native collagen.

Example 2: Mass Spectrometric Detection of TE16C Protein

Experimental Method

| | |
|---|---|
| Instrument name | Matrix-assisted laser desorption ionization-time-of-flight mass spectrometer MALDI-TOF/TOF Ultraflextreme ™, Brucker, Germany |
| Matrix | CHCA Laser energy 125 |
| Data retrieval software | Mascot Retrieval species ALL entries |
| Retrieval database | NCBIprot |

The protein sample was subjected to DTT reduction and alkylation of iodoacetamide, and then trypsin was added to digest overnight. The peptide segment obtained after enzymolysis was desalted by C18 ZipTip and then mixed with matrix α-cyano-4-hydroxycinnamic acid (CHCA) for spotting. Finally, the matrix-assisted laser desorption ionization—time-of-flight mass spectrometer MALDI-TOF/TOF Ultraflextreme™, Brucker, Germany was used for analysis (for the technique of peptide fingerprinting, see: Protein J. 2016; 35: 212-7, which is incorporated herein by reference).

Database retrieval was handled through the MS/MS Ion Search page on the local mascot website. The protein identification results were obtained based on the primary mass spectrum of the peptide segments produced after enzymolysis. Retrieval parameters: trypsin enzymolysis, set two missed restriction sites. The alkylation of cysteine was set to a fixed modification, and the oxidation of methionine was set to a variable modification. The database used for the identification is NCBprot.

The mass spectrometry peak results are shown in FIG. 1.

TABLE 1

Mass spectrometry detection of molecular weight and corresponding peptide

| Observed value | Mr (Expected value | Peptide |
|---|---|---|
| 2246.2323 | 2246.1424 | GAPGERGAPGFRGPAGPNGIPGEK |
| 2246.2323 | 2246.1424 | GAPGFRGPAGPNGIPGEKGPAGER |
| 1738.8731 | 1738.9095 | GPAGERGAPGERGAPGFR |
| 1678.9003 | 1678.8659 | GAPGFRGPAGPNGIPGEK |
| 1660.8401 | 1661.8607 | GPAGPNGIPGEKGPAGER |
| 1171.5966 | 1171.6295 | GAPGERGAPGFR |
| 1093.5636 | 1093.5784 | GPAGPNGIPGEK |

Coverage of the peptide fragment detected

GER<u>GAPGFRGPAGPNGIPGEKGPAGERGAPGERGAPGFRGPAGPNGIPGE</u>

<u>GERGAPGFRGPAGPNGIPGEKGPAGERGAPGERGAPGFRGPAGPNGIPGE</u>

<u>KGPAGERGAPGERGAPGFRGPAGPNGIPGEKGPAGERGAPGERGAPGFRG</u>

<u>PAGPNGIPGEKGPAGERGAPGERGAPGFRGPAGPNGIPGEKGPAGERGAP</u>

<u>GERGAPGFRGPAGPNGIPGEKGPAGERGAPGERGAPGFRGPAGPNGIPGE</u>

<u>KGPAGERGAPGERGAPGFRGPAGPNGIPGEKGPAGERGAPGERGAPGFRG</u>

<u>PAGPNGIPGEKGPAGERGAPGERGAPGFRGPAGPNGIPGEKGPAGERGAP</u>

<u>GERGAPGFRGPAGPNGIPGEKGPAGER</u>GAP

More than 98.8% of the sequence of the protein TE16C to be determined can be detected by mass spectrometry, and the results are very reliable. The mass spectrometric characteristic peaks of the undetermined protein were 2246.2323, 2246.2323, 1738.8731, 1678.9003, 1660.8401, 1171.5966, and 1093.5636, and it was concluded that the TE16C protein was correctly expressed.

Example 3: Detection of Properties of Recombinant Type III Collagens

Methods for detecting collagen activity can be found in the reference Juming Yao, Satoshi Yanagisawa, Tetsuo Asakura, Design, Expression and Characterization of Collagen-like Proteins Based on the Cell Adhesive and Cross-linking Sequences Derived from Native Collagens, *J Biochem*. 136, 643-649 (2004), which is incorporated herein by reference. The specific implementation method is as follows:

1. The concentrations of the protein samples to be tested were measured by ultraviolet absorption method, including control human collagen (Sigma, C7774), control old type III collagen HC16, new type III collagen TE16C protein, control T16a protein and T16b protein samples. Specifically, the respective ultraviolet light absorption of the samples at 215 nm and 225 nm was measured, and the respective protein concentration was calculated using the empirical formula $C (\mu g/mL) = 144 \times (A215 - A225)$, and it should be noted that the detection was performed under the condition of $A215 < 1.5$. The principle of the method is to determine the characteristic absorption of a peptide bond under far ultraviolet light, and the method is not affected by chromophore content, has few interfering substances, is easy to operate, and is suitable for detecting human collagen and its analogs which are not colored by Coomassie Brilliant Blue. (Reference is Walker J M., The Protein Protocols Handbook, Second edition, Humana Press, 43-45, which is incorporated herein by reference) After protein concentration detection, all the concentrations of the proteins to be tested were adjusted to 0.5 mg/mL with PBS.

2. 100 μL of each protein solution was added to a 96-well plate and compared with a blank PBS solution, and allowed to stand at room temperature for 60 min.

3. $10^5$ well-cultured 3T3 cells (from Teacher Tong Pei, Tsinghua University) were added to each well and incubated at 37° C. for 60 min.

4. Each well was washed 4 times with PBS.

5. The absorbance of OD492 nm was measured using an LDH assay kit (Roche, 04944926001). Based on the value of the blank control, the attachment rate of cells can be calculated. The calculation formula is as follows: cell adherence rate=(test well−blank well)×100%/(positive well−blank well). The adherence rate of the cells can reflect the activity of collagen. The higher the activity of a protein, the faster it can provide a cell with a superior external environment to help the cell adhere.

Figure 2:
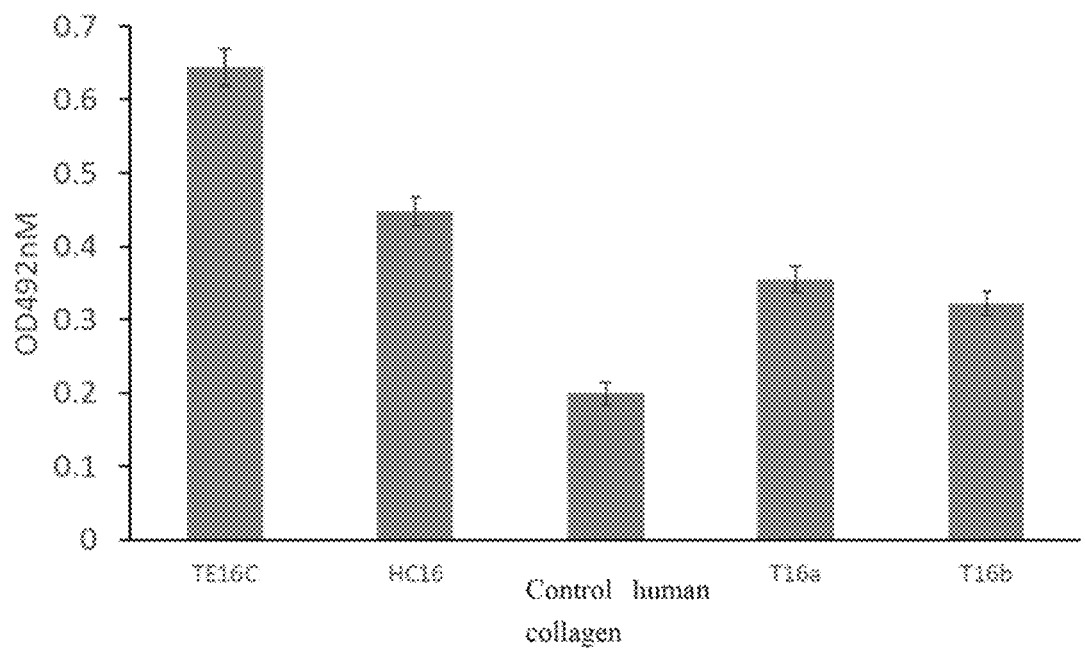
FIG. 2: Comparison of cell adhesion activities between different recombinant type III collagens.

See FIG. 2 for the results.

The results in FIG. 2 indicate that the two human recombinant collagens (i.e., type III collagen HC16 and type III collagen TE16C) have better adhesion activities than commercial human collagen, and the recombinant type III collagen TE16C of the present invention achieves the most potent cell adhesion activity. The proteins obtained by the two construction methods of T16a and T16b as controls have lower cell adhesion activities than the TE16C protein of the present invention.

Example 4: Expression and Purification of Recombinant Type III Collagens

TE16C Protein Expression and Purification

1. According to steps 1-5 in Example 1, the collagen of interest TE16C separated from the vector protein was obtained and dialyzed into solution A (10 mM $Na_2CO_3$, pH 10.5, 10 mM NaCl) of an anion exchange column.

2. The anion exchange column (Hitrap Q HP column, 5 mL, GE Healthcare Biosciences) was equilibrated with 5 column volumes of solution A (10 mM $Na_2CO_3$, pH 10.5, 10 mM NaCl). The dialyzed TE16C protein was then applied to the column, and the protein peak that had passed through the column, i.e. the purified TE16C protein, was collected. The resulting product was dialyzed overnight and lyophilized to dry powder for use.

3. The anion exchange column was eluted with 5 column volumes of solution B (10 mM $Na_2CO_3$, pH 10.5, 1 M NaCl) to wash out the impurity proteins and endotoxin from the column.

The HC16 protein, the polypeptide T16a comprising repeat sequences and a C-terminal stable sequence, and the polypeptide T16b comprising repeat sequences and linker amino acids were treated in the same manner.

Figure 3:
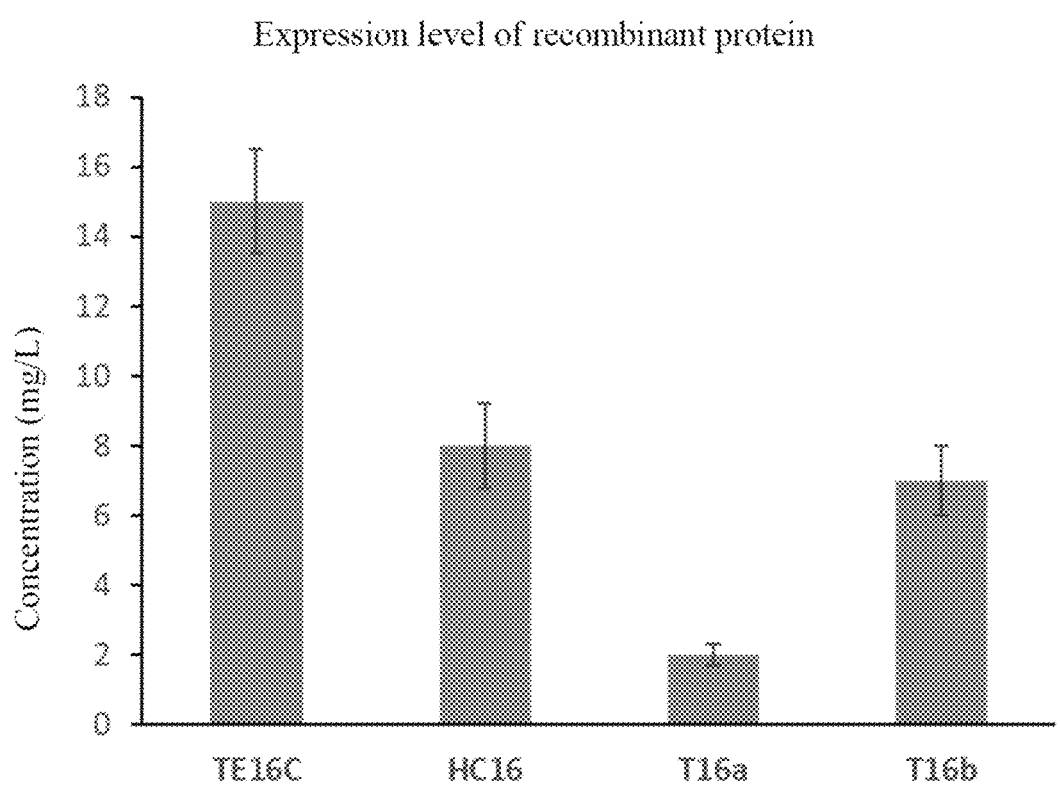
FIG. 3: Cell expression levels of different recombinant type III collagens.

FIG. 3 shows the expression of recombinant type III collagens. After the purification of the type III collagen HC16, about 8 mg of pure protein can be obtained from 1 L of the bacterial solution. After the purification of the type III collagen TE16C, about 15 mg or more of pure protein can be obtained from 1 L of the bacterial solution. The expression levels of the proteins obtained by the two construction methods of T16a and T16b as controls were also not as high as that of the TE16C protein of the present invention. It is important to note that for the construction method of T16a, the amount of soluble protein in the supernatant is very low because of the formation of a large amount of colloid during the purification of the protein.

Figure 4:
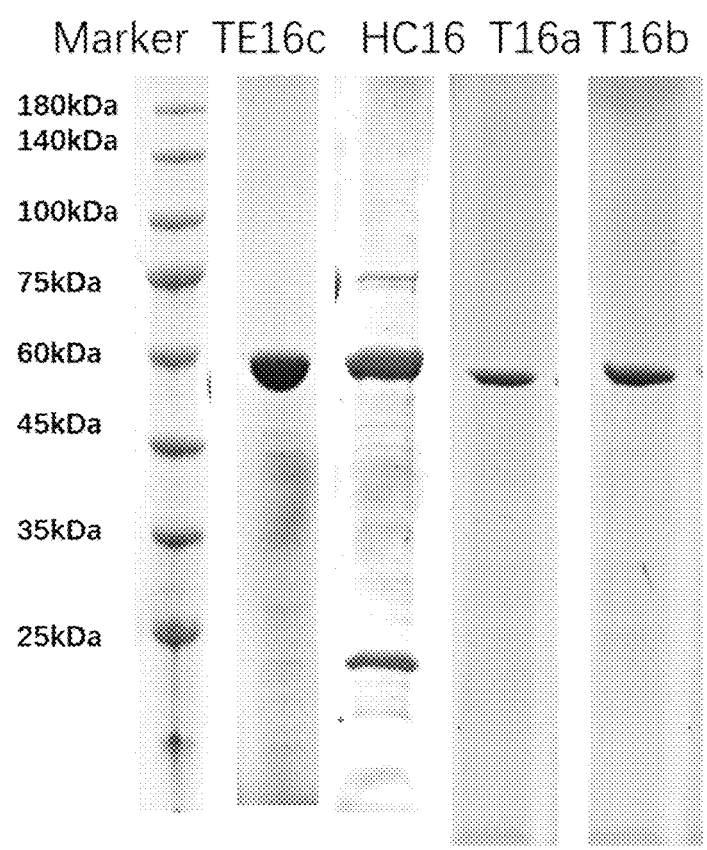
FIG. 4: Purification of different recombinant type III collagens.

FIG. 4 shows the purification of recombinant type III collagens. The type III collagen HC16 had a purity of about 95% after Ni column and anion exchange column, while the type III collagen TE16C could be rapidly purified to a purity of more than 99% by a Ni column and an anion exchange column. Though the proteins obtained by the two construction methods of T16a and T16b as controls had high purities, their yields were not high and were much lower than the TE16C protein of the present invention.

Example 5: Stabilization of Recombinant Type III Collagens in Aqueous Solutions

Stability Study

1. The purified TE16C protein and HC16, T16a and T16b proteins were obtained according to Example 4 and then dialyzed against physiological saline (0.9% NaCl). The dialyzed protein solutions were collected, sterilized by filtration through a 0.22 µM filter membrane, and then allowed to stand for a long time in an environment of 4-8° C.

2. At different time points, such as one month, two months, three months, half a year, one year, aqueous solutions of TE16c protein and HC16 protein were collected, and were measured for purity by SDS-PAGE (see the method of Example 1).

Figure 5:
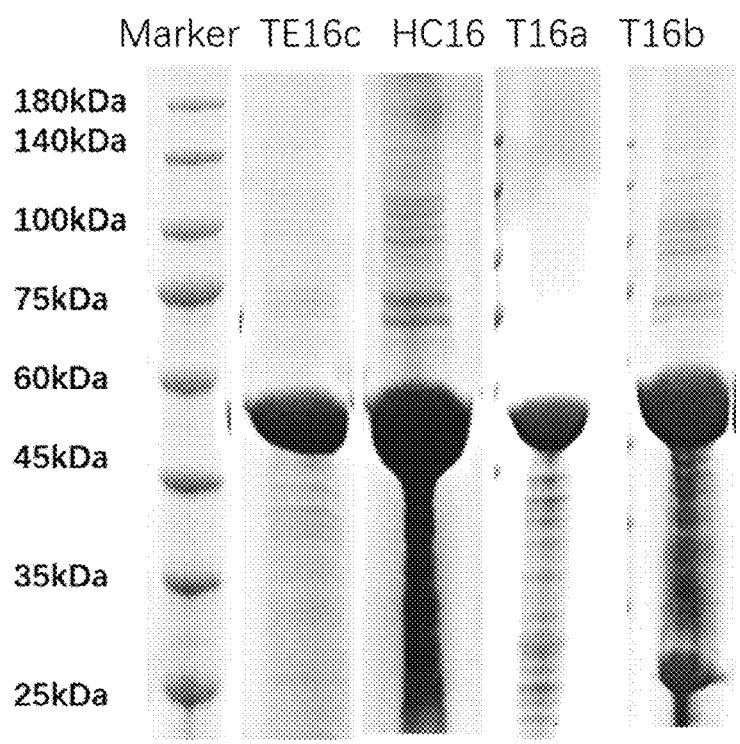
FIG. 5: Stability of different recombinant type III collagens.

FIG. 5 shows the electrophoresis images of HC16, TE16C, T16a and T16b at the time point of half a year. The type III collagen HC16 was unstable in the aqueous solution, significant degradation occurred after one month, and degradation after six months was very serious. However, the type III collagen TE16C has a stable structure, and after being placed in an aqueous solution for half a year, more than 90% of the protein remained as a complete full-length protein, and only a small amount was degraded. The proteins obtained by the two construction methods of T16a and T16b as controls also had different degrees of degradation, with the degradation of T16b being more serious; their stability is much lower than that of the TE16C protein of the present invention.

Example 6: Detection of Endotoxin in Recombinant Type III Collagens

Endotoxin Detection of TE16c Protein, HC16 Protein, T16a Protein and T16b Protein 1. Purified TE16c protein, HC16 protein, T16a protein and T166 protein were prepared according to Example 4.

2. Reagents including tachypleus amebocyte lysate (Zhanjiang A&C Biological Ltd., λ=0.015 EU/ml) and diluent I (Zhanjiang A&C Biological Ltd.) were prepared.

3. The endotoxin standards were diluted to E1, E0.5, E0.25, E0.125, and E0.0625. The samples were diluted 5, 8, 16, 32, 50, 100, 200, 300 and 400 times with diluent I, and the other samples were diluted with water for detection, to dilute the samples 10, 16, 32, 64, 100, 200, 400, 600 and 800 times, respectively.

4. The endotoxin standards and the diluted protein samples were added to the tachypleus amebocyte lysate for observation. The results were compared to both negative and positive controls. The endotoxin concentrations of the samples were calculated.

Figure 6:
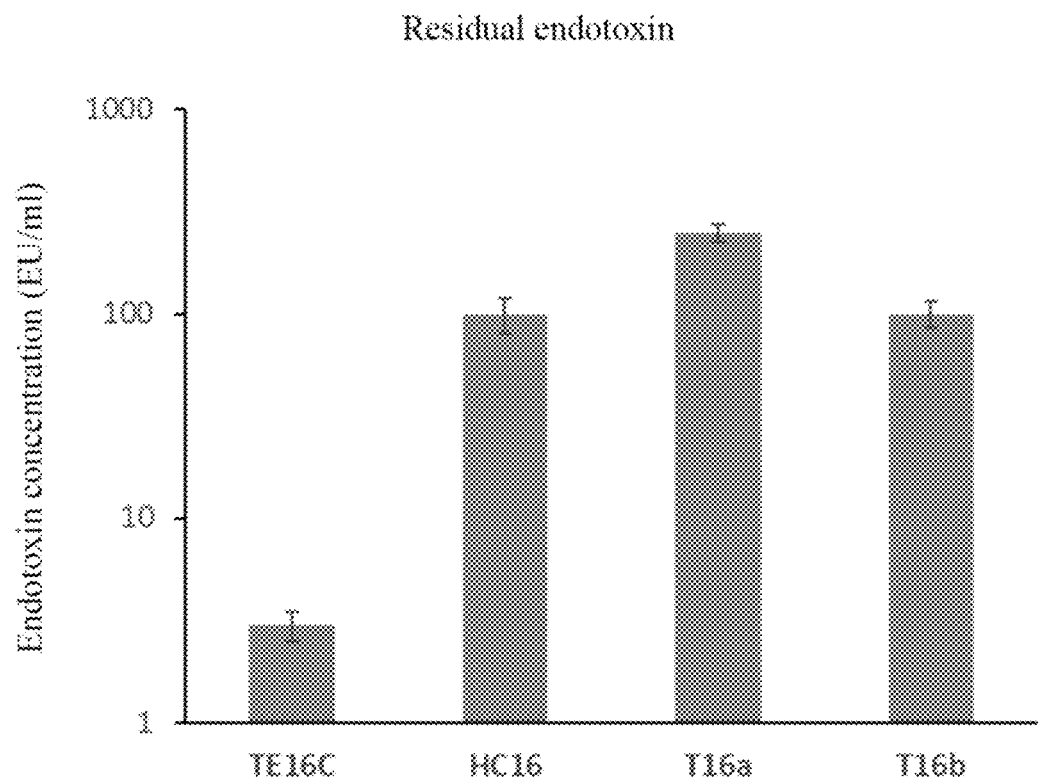
FIG. 6: Residual endotoxin of different recombinant type III collagens.

FIG. 6 shows the residual endotoxin status of recombinant type III collagens. The type III collagen HC16 is not uniform in structure and is easy to bind to endotoxin, so the residual endotoxin after Ni column and anion exchange is about 100 EU/mL, while the new type III collagen TE16C can be rapidly purified to contain less than 5 EU/mL of endotoxin by a Ni column and an anion exchange column. The proteins obtained by the two construction methods of T16a and T16b as controls are also tightly bound to endotoxin, and it is not easy to remove endotoxin.

Example 7: Analysis of Recombinant Type III Collagens

1. The sequence of TE16C contains the segment of the human type III collagen Pro488 to Gly510, and several polypeptides (Taihe Biotechnology Co., Ltd., Beijing) were synthesized based on this regional sequence for extensive crystal screening, e.g., GFRGPAGPNGIPGEKGPAGERG polypeptide.

2. The polypeptide was dissolved in water to a solution of 15 mg/mL, and crystals were grown by a hanging drop method in which the formulation of tank solution was 30% (w/v) PEG 400, 0.1 M Na Acetate pH 4.6, and 0.1 M Cadmium Chloride. 1 µL of each of the polypeptide solution and the tank solution were taken and mixed, and then sealed with 1 mL of the tank solution.

3. After about one week, single crystals of the polypeptide gradually grew in the droplet, and was quickly cooled and stored with liquid nitrogen after being taken out.

4. The collected polypeptide crystals were sent to the BL-18U1 Beamline of Shanghai Synchrotron Radiation Facility for X-ray crystal diffraction data collection, and at the same time the data analysis and structure analysis were carried out using the calculator of the line station.

Figure 7:
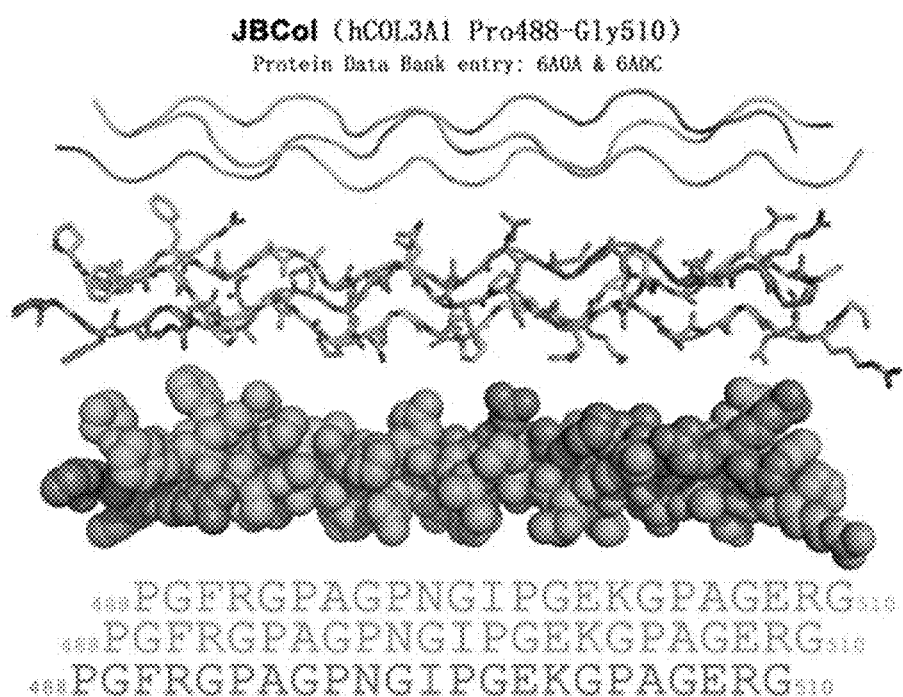
FIG. 7: Structure analysis of recombinant type III collagen TE16C.

We obtained the high-resolution three-dimensional structure of the human type III collagen Pro488 to Gly510 region contained in the new type III collagen TE16C by the method of protein crystallography, as shown in FIG. 7. It was confirmed that this region formed a very stable trimer structure. Therefore, the structure and function of intact collagen can be possessed without additionally adding the C-terminal sequence of GPPGPCCGGG.

The invention claimed is:

1. A polypeptide comprising 16 repeats of the sequence set forth in SEQ ID NO: 1, wherein the repeats of the sequence are directly linked and wherein the polypeptide does not comprise the sequence set forth in SEQ ID NO: 2 and comprises the amino acid sequence of SEQ ID NO:3.

2. A composition comprising the polypeptide according to claim 1.

3. The composition according to claim 2, wherein said composition is a medical device, a tissue engineering product, a cosmetic or a health care product.

4. The composition according to claim 2, wherein said polypeptide is in the form of an aqueous solution of the polypeptide.

5. The composition according to claim 2, wherein the composition is free of a component that prevents degradation of the polypeptide.

6. The polypeptide according to claim 1, further comprising an amino acid sequence of SEQ ID NO: 4.

7. A method of manufacturing, comprising incorporating the polypeptide according to claim 1 into a composition, wherein the composition is a medical device, a tissue engineering product, a cosmetic, or a health supplement, wherein the polypeptide is in the form of an aqueous solution of the polypeptide, and the composition is free of a component that prevents degradation of the polypeptide.

8. A method of promoting cell adhesion by a cell, the method comprising contacting the cell with the polypeptide according to claim 1.

* * * * *